(12) United States Patent
Devergne et al.

(10) Patent No.: US 8,267,308 B2
(45) Date of Patent: Sep. 18, 2012

(54) FLUID PROCESSING MEDICAL APPARATUS AND METHOD FOR SETTING-UP A FLUID PROCESSING MEDICAL APPARATUS

(75) Inventors: Jacky Devergne, Littleton, CO (US); Nicolas Goux, Craponne (FR); David Nepote-Vesino, Jonage (FR); Michele Stefanini, Mirandola (IT); Giulio Guaitoli, Carpi (IT); Gianni Borsari, Medolla (IT)

(73) Assignee: Gambro Lundia AB, Lund (SE)

( * ) Notice: Subject to any disclaimer, the term of this patent is extended or adjusted under 35 U.S.C. 154(b) by 233 days.

(21) Appl. No.: 12/596,070

(22) PCT Filed: Jun. 19, 2007

(86) PCT No.: PCT/IB2007/001646
§ 371 (c)(1),
(2), (4) Date: Apr. 20, 2010

(87) PCT Pub. No.: WO2008/129344
PCT Pub. Date: Oct. 30, 2008

(65) Prior Publication Data
US 2010/0282834 A1 Nov. 11, 2010

(30) Foreign Application Priority Data
Apr. 19, 2007 (FR) .................................. 07 02823

(51) Int. Cl.
*G06F 17/00* (2006.01)
(52) U.S. Cl. ........................................ 235/375; 235/435
(58) Field of Classification Search .................. 235/375, 235/382, 376, 435; 715/744
See application file for complete search history.

(56) References Cited

U.S. PATENT DOCUMENTS

| | | | |
|---|---|---|---|
| 5,658,456 A | 8/1997 | Kenley et al. |
| 5,769,811 A | 6/1998 | Stacey et al. |
| 6,626,355 B2 | 9/2003 | Sasse et al. |
| 6,685,831 B2 | 2/2004 | Donig et al. |
| 2002/0038392 A1 | 3/2002 | De La Huerga |
| 2003/0088203 A1 | 5/2003 | Gelfand et al. |
| 2006/0167400 A1 | 7/2006 | Ellingboe et al. |
| 2006/0200369 A1 | 9/2006 | Batch et al. |
| 2006/0219792 A1 | 10/2006 | Zhu et al. |

FOREIGN PATENT DOCUMENTS

| | | |
|---|---|---|
| DE | 32 37 016 A1 | 5/1983 |
| DE | 201 13 789 U1 | 5/2002 |
| EP | 0 341 799 A2 | 11/1989 |
| EP | 0 491 981 A1 | 7/1992 |

(Continued)

OTHER PUBLICATIONS

Fresenius Medical Care, "Genius® 90 Therapy System for acute and chronic haemodialysis", 732 754 1/3 GB (2 g/h/b 05.04), 2004,12 pages.

(Continued)

*Primary Examiner* — Edwyn Labaze
(74) *Attorney, Agent, or Firm* — Pearne & Gordon LLP

(57) ABSTRACT

The invention relates to a method for setting up a fluid treatment apparatus using a single, and always accessible, reader of information relating to replaceable components which are to be mounted on the apparatus to perform the fluid treatment. It is also disclosed a fluid treatment apparatus having the always accessible reader. The reader can also be relied on to enter information other that those relating to the replaceable components, such as commands for the apparatus, patients' related information, etcetera.

50 Claims, 15 Drawing Sheets

FOREIGN PATENT DOCUMENTS

| | | | |
|---|---|---|---|
| EP | 0 771 569 | A2 | 5/1997 |
| EP | 1 170 023 | A2 | 1/2002 |
| EP | 1 576 972 | A2 | 9/2005 |
| GB | 2 110 564 | A | 6/1983 |
| WO | 80/02376 | A1 | 11/1980 |
| WO | 99/10028 | A1 | 3/1999 |
| WO | 01/41831 | A2 | 6/2001 |
| WO | 02/095675 | A1 | 11/2002 |
| WO | 03/026724 | A1 | 4/2003 |
| WO | 2004/033024 | A1 | 4/2004 |
| WO | 2004/062710 | A2 | 7/2004 |
| WO | 2005/118054 | A1 | 12/2005 |
| WO | 2006/086701 | A1 | 8/2006 |
| WO | 2007/118235 | A2 | 10/2007 |
| WO | 2007/144427 | A2 | 12/2007 |

OTHER PUBLICATIONS

C. Cerrato, E. Gatti et al., "Ottimizzazione dell'organizzazione di un Centro Dialisi tramite utilizzo di Sistemi Informativi", Rendiconti 94a Riunione Annuale AEI, vol. 6, Ancona, 03.-06. Ottobre 1993, Associazione Elettrotecnica ed Elettronica Italiana, pp. 27-30 (12 pages).

Bondi Emanuele, Library Manager—Department of Electrical Engineering, "Confirmation Letter", Politecnico di Milano, Italy, Mar. 20, 2012, one page.

FLUID PROCESSING MEDICAL APPARATUS AND METHOD FOR SETTING-UP A FLUID PROCESSING MEDICAL APPARATUS

FIELD OF THE INVENTION

The invention relates to a fluid processing medical apparatus such as an extracorporeal blood treatment apparatus for performing one or more of the following treatments: ultrafiltration, hemodialysis, hemodiafiltration, hemofiltration, plasmapheresis, oxygenation, or other procedures on whole blood or on blood components, such as separation or collection of blood or blood components. The invention also concerns a method for setting-up a fluid processing medical apparatus.

BACKGROUND OF THE INVENTION

Blood processing apparatus such as extracorporeal blood treatment machines comprise a number of components which have a use limited in time or in the number of use cycles. In the present specification, the following definitions assume the meaning below indicated:
- disposables are those components which can be associate to the processing apparatus for the duration of a single procedure or treatment (i.e. single use components)
- semi-disposables are those components which can be associate to the processing apparatus for the duration of a limited number of procedures or treatments (i.e. components designed to be used a limited number of times).

Depending upon the situations, components such as filters (hemo-dialyzers, hemo-filters, ultrafilters and the like), solutions bags, containers hosting liquids or powders for preparation of treatment liquids, tubing sets, extracorporeal blood circuits, integrated modules including a number of the components just mentioned could be used as disposables or semi-disposables.

Before the medical apparatus, e.g. a blood treatment machine, has to execute a treatment session, the operator shall setup the machine and install all appropriate disposable components suitable for running the selected treatment procedure. The operator also checks if one or more semi-disposable components need to be changed.

Referring for instance to a blood treatment for treating patients suffering from kidney failure, before any procedure starts the operator should normally install the filter, the bloodlines, the access devices adequate for the treatment session. The operator also installs the appropriate concentrates and solutions to be used during the treatment, checks and/or changes the ultrafilters in the liquid preparation circuit (in case on-line liquid preparation is selected).

For the purpose of disclosure of the present invention disposables and semi-disposable components are hereinafter globally referred to as replaceable components.

As it can be easily understood the blood treatment apparatus shall be properly instructed as to which specific replaceable components are installed because each component has specific properties which may affect the working of the apparatus and the direct or indirect delivery to the patient of substances.

During the past years, in order to facilitate setup procedures, those replaceable components to be mounted on the treatment apparatus have been provided with indicia (such as bar codes, color codes, microchips, RFID devices, mechanical keys, etcetera) secured to the component and detectable by a respective appropriate reader associated to the treatment apparatus to provide the apparatus at least with an information relating to the identity of the same component.

Here below the technical solutions which the applicant regards as relevant are described.

A first solution is disclosed in WO80-02376 which describes a hemodialysis system using disposables tubing and filter having optical or magnetic coding indicia on a strip. The strip can be coded to match a specific program or procedure, and the system can be constructed or programmed to generate a signal should the module and the program in the system not correspond.

U.S. Pat. No. 5,769,811 shows a blood processing machine and disposable units for use therewith. The disposable units generally comprise a centrifuge bowl for separating whole blood into blood constituents, an inlet tube for conveying blood into the bowl, an outlet tube for conveying the blood constituents away from the bowl, and a manifold for placing the inlet tube and the outlet tube in fluid communication with a tube from a donor. The manifold has a machine-readable bar-code label for identifying to the blood processing machine which type of disposable unit is being coupled to it. The machine itself comprises a central processing unit that controls overall operation, a first computer memory containing safety-monitoring instructions that cause the central processing unit to monitor various state parameters in order to ensure donor safety, and a second computer memory containing instructions that define at least one apheresis or blood-processing protocol. In some implementations, the second computer memory is removable from and insertable into the blood processing machine by an operator.

U.S. Pat. No. 6,626,355 discloses a medical apparatus comprising an accessory port and at least one accessory piece comprising a connection element complementary to said accessory port; the connection element includes a storage unit where coded and/or un-coded information is stored, is read by means of a readout unit disposed in the section of said accessory port, and is compared to identification information stored in readout unit; the medical device is activated when the identification information match the desired identification information, and is blocked when the identification information do not match. Coded identification information is decodable by means of a proprietary key.

EP1170023 concerns a hemodialysis machine comprising at least one semi-permanent component, such as an ultrafilter for use in the online preparation of dialysis liquid. The component is changed periodically after being used for several consecutive dialysis treatments; the machine comprises a bar-code reader for identifying the semi-permanent components thus unequivocally identifying the semi-permanent component mounted on the machine, and communicating its presence and identity to said control unit in the machine.

U.S. Pat. No. 6,685,831 discloses a dialysis machine with a device for preparing dialysis solutions. Preparation of dialysis fluids of different concentrations is achieved by the fact that the device has a detector device, at least two connections and at least two interchangeable storage containers to hold the solution ingredients to be metered. Each container is connected to at least one connector, and the connectors are connectable to the connections; the connectors or the areas of a connecting tube near the connectors have identification means which can be detected by the detector device. It is also disclosed a connector for connecting a storage container with solution ingredients to a medical apparatus, where the connector or areas of a connecting tube near the connector has identification means. Detecting a connection of a solution ingredient storage container is guaranteed by the fact that the connector is provided with identification means and is attached to a matching component, and a reader unit determines the type and position of the connector.

WO01/41831 discloses a hemofiltration machine including a chassis, at least one flow controlling element on the chassis, and a controller for the hemofiltration machine to operate the flow controlling element to carry out a processing task in response to a control program, the controller including an input on the chassis for reading coded indicia, an extracorporeal circuit for circulating blood from an individual through a hemofilter, and a fluid processing cartridge holding the extracorporeal circuit for mounting as an integrated unit on the chassis in operating engagement with the flow controlling element and for removal as an integrated unit from the chassis, the fluid processing cartridge carrying coded indicia incorporating a control program for the controller, the coded indicia being readable by the input in response to mounting the fluid processing cartridge on the chassis, to thereby transfer the control program to the controller for execution. Document WO2004033024 shows a medical-technical identification device for identifying a sterile product for example a product intended for one-time-use only, when connected to a piece of medical equipment. The sterile product includes a fixedly mounted information carrier which is adapted to deliver or to offer specific product information in a contactless fashion to a reading element connected to the equipment.

U.S. Pat. No. 5,658,456 describes a dialysis apparatus having a dialysate preparation module and a tank for storing a dialysate solution, for performing automatic verification of dialysate chemicals prior to adding said chemicals to said dialysate preparation module so as to insure correct preparation of said dialysate solution, comprising: an electronic reader of a machine-readable indicator, said electronic reader incorporated into said dialysis machine; a bottle containing a unit batch of dialysate chemicals for treatment of a medical condition of a patient to be treated by said dialysis machine, said bottle adapted to be installed on an opening apparatus in said machine such that, when said bottle is opened, said dialysate chemicals are placed in fluid communication with said tank for delivery of said unit batch of dialysate chemicals automatically into said tank; and a machine-readable indicator containing coded information (ID,LOT,DATE) as to said dialysate chemicals contained in said bottle, said machine-readable indicator applied to said bottle in a manner for permitting machine identification of the contents of said bottle by said electronic reader prior to operating the opening apparatus to open said bottle and adding said dialysate chemicals to said tank, whereby machine identification of said dialysate chemicals contained in said bottle may occur prior to introduction of said chemicals into said tank.

SUMMARY OF THE INVENTION

While numerous solutions have been provided, the applicant has envisaged a new method and a new apparatus which are suitable for further improving machine setup and data entry of information when replaceable components are used.

Indeed, according to the technical solutions of the prior art, the treatment apparatus had a respective reader located in correspondence of the position where the disposable or semi-disposable article is expected to be mounted on.

This situation renders impossible accessing the reader while a disposable or semi-disposable is already installed.

Moreover in case a plurality of disposable or semi-disposable components have to be installed in different locations of the apparatus, then a corresponding number of readers would be required.

Furthermore the reader of replaceable devices ID according to the prior art is only used for a single purpose and cannot be relied on for entering commands or other data into the medical apparatus.

In view of this situation it is a goal of the present invention to provide a fluid processing medical apparatus and method for transferring data to a fluid processing medical apparatus capable of enhancing setup procedures and, more in general, transfer of data to the medical apparatus.

It is a further object of the invention to reduce the number of readers to be present on the medical apparatus side without impairing on the ease and data entry reliability.

The above aims are reached by a method for setting-up a fluid processing medical apparatus, the apparatus being of the type comprising:

a support structure for receiving a plurality of replaceable components of different categories in correspondence of respective operating areas of said apparatus, at least a user interface for enabling setting of a plurality of parameters pertinent to operation of said apparatus or pertinent to a process to be performed by said apparatus, the user interface including at least a screen, the method comprising the following steps:

providing a reader having a reading portion for reading information concerning the components, the reading portion being distinct and spaced from said operating areas and accessible for reading the information irrespective of the components being engaged or not with apparatus, reading the information of a new component to be installed on the apparatus by relatively approaching the reading portion to a carrier of said new component information, coupling the new component with the apparatus in correspondence of a respective of said operating areas, the component when coupled leaving the reading portion accessible for reading the information.

According to an aspect of the invention, after the reading step it is provided a step of verifying if the new component is of the same category of a component already installed on the machine. In other words if for instance the new component is a concentrate container, such as a bicarbonate cartridge, the method provides for checking if a bicarbonate cartridge was already installed on the apparatus. In practice the verifying step can be done by checking if a component having the same category of the new component has been already read before and/or by checking if a component is engaged with the engaging means of the type adapted to receive the new component.

The steps of reading and verifying can be repeated every time a new component is to be coupled to the apparatus.

The replaceable components are a plurality of components of different categories (by way of non limiting example a plurality of filters, a plurality of concentrate cartridges, a plurality of bloodlines, etcetera), where each component of a same category having respective mechanical connection to a corresponding operating area on the apparatus, different from that of components of other categories. The medical apparatus includes a plurality of different types of engaging means, each type of engaging means being designed for mechanically engaging, in a respective operating area, a component of one corresponding category only.

In an embodiment, the method includes the sequential steps of:

signaling that a component of the same category is already installed on the apparatus requesting for confirmation to substitute the installed component with the new component, initiating a procedure for substitution of the installed component with the new component.

According to a further aspect of the invention, for instance before coupling each new component to the apparatus, the method provides for:

selecting a desired treatment procedure (for instance in case the apparatus is a blood treatment machine, the method provides for selecting among a plurality of treatments such as hemofiltration, ultrafiltration, hemodiafiltration, hemodialysis etcetera), checking if the new component fits with the selected treatment procedure, signaling if the new component does not fit with the selected treatment procedure.

While in one embodiment the information is fixed to the replaceable component, the information carrier could also be the packaging of the component or a card associated with the component.

According to a further aspect the reader can be relied on for entering commands into the apparatus by associating command information to a readable information carrier, relatively approaching to one another the information carrier and the reading portion to enter the command in the apparatus, initiating a treatment procedure complying with the entered command.

According to another embodiment the reader can be relied on for entering commands into the apparatus by associating patient data information to a readable information carrier, relatively approaching to one another the information carrier and the reading portion to enter the command in the apparatus.

In addition to the above way of entering component related information and initiating a substitution procedure of a replaceable component, the method of the invention provides for an additional and parallel procedure for installing a new replaceable component on the apparatus without interacting with said reader.

This additional procedure includes the following steps:

entering the information of a new component to be installed on the apparatus by acting on said user interface, verifying if the new component is of the same category of a component already installed on the machine, displaying on said screen a message informing if a component of the same category is already installed, in case a component of the same category is already installed asking for confirmation to proceed with the substitution thereof, coupling the new component with the apparatus in correspondence of a respective of said operating areas, the component when coupled leaving the reading portion accessible for reading the information.

In case a component of the same category is already present the method can also provide for the following steps: moving the installed component from an operating condition to a non-operating condition where it can be safely disengaged from the apparatus, and then disengaging said component before installing the new one.

The step of entering information by acting on the user interface comprises the steps of:

Configuring the user interface as a plurality of displays, each display being accessible to the operator and including information corresponding to at least a respective replaceable component (this can be done with a navigation keyboard or keypad either part of the screen or external, which allows the user to navigate through various displays stored in the memory of the user interface control system), Selecting the desired display of the user interface, Selecting the new component to be installed by acting on said selected display.

The user interface can also be used to enter commands without acting on said reader and/or to enter patient related information again without acting on said reader.

The above specified aims are also reached by a fluid processing medical apparatus, comprising:

a support structure, a plurality of replaceable components of different categories engaged to the support structure in correspondence of respective operating areas, at least a user interface enabling setting of a plurality of parameters pertinent to operation of said apparatus or pertinent to a process to be performed by said apparatus, the user interface including at least a screen, a reader, distinct from said user interface, having a reading portion for reading information concerning the components, the reading portion being spaced from said operating areas and accessible for reading the information irrespective of the components being engaged or not to the support structure, a control system for controlling operation of said medical apparatus and responsive to actions by a user on said user interface, said control system also communicating with the reader and being programmed for receiving and storing at least said information concerning the components every time the reader reads information concerning a new component to be installed on the apparatus.

In practice the control system includes means for controlling the apparatus operation (a network of sensors, actuators and connections not further detailed as their nature is not relevant for the purpose of present invention), means for receiving and storing information coming from and/or going to the user interface and means for receiving and storing information coming from the reader (i.e. wired or wireless connections to the reader, a control processing unit of digital or analogical type and a memory).

In one embodiment the control system is programmed (i.e. comprises means in the form of an analogical circuit portion or in the form of a suitably programmed digital processor) for verifying if the new component is of the same category of a component already installed on the apparatus. The above steps of reading and verifying can be automatically repeated anytime the reader reads information of a new component to be installed. In one embodiment the step of verifying includes determining the category of the new component, and/or checking if a component of the same category was detected before, and/or checking if a component is engaged with the engaging means of the type adapted to receive the components of the category of the new component.

The replaceable components are a plurality of components of different categories (by way of non limiting example a plurality of filters, a plurality of concentrate cartridges, a plurality of bloodlines, etcetera), where each component of a same category having respective mechanical connection to a corresponding operating area on the apparatus, different from that of components of other categories. The medical apparatus includes a plurality of different types of engaging means, each type of engaging means being designed for mechanically engaging, in a respective operating area, a component of one corresponding category only.

According to one aspect of the invention, the control system is also programmed (i.e. comprises means in the form of an analogical circuit portion or in the form of a suitably programmed digital processor) for sequentially executing the following steps:

signaling that a component of the same category is already installed on the apparatus, requesting for confirmation to substitute the installed component with the new component, initiating a procedure for substitution of the installed component with the new component.

In accordance with a further aspect of the invention, the control system is programmed for executing the following steps:

receiving selection of a desired treatment procedure, checking if the new component fits with the selected treatment procedure, signaling if the new component does not fit with the selected treatment procedure, allowing the step of coupling the new component with the apparatus only after the step of checking if the new component fits with the selected treatment procedure.

According to an embodiment of the invention, the information comprises one or more selected in the group including:

Identity of the component,

Identity of a series of identical components (this can happen in case a series of component shares same identical characteristics), Expiration date of the component, Manufacturer, One or more commands for programming the apparatus to execute a procedure on said fluid, Data concerning a patient (pressure measures made before treatment, prescription, personal information)

The information carrier is one selected in the group comprising: a surface of the component, a packaging of the component, a card associated with the component.

The apparatus of the invention can also have the control system programmed for receiving commands for carrying out a corresponding procedure on said fluid and/or patient data by reading corresponding information associated to a readable information carrier which is approached to the reading portion.

In addition to the reader, the control system can also be programmed for executing an additional procedure for installing a new replaceable component on the apparatus without interacting with said reader, the additional procedure comprising the steps of:

allowing to enter information of a new component to be installed on the apparatus by acting on said user interface, verifying if the new component is of the same category of a component already installed on the machine, displaying on said screen a message informing if a component of the same category is already installed, coupling the new component with the apparatus in correspondence of a respective of said operating areas, the component when coupled leaving the reading portion accessible for reading the information.

The step of allowing entering information by acting on the user interface can comprise the steps of:

Configuring the user interface as a plurality of displays, each display being accessible to the operator and including information corresponding to at least a respective replaceable component, Allowing selecting the desired display of the user interface, Allowing selecting the new component to be installed by acting on said selected display.

In practice the reader used in the invention can be any optical reader (bar code reader, or color code reader, or reader of any optically detectable shape and/or pattern) or a radio-frequency reader (RFID reader) or magnetic reader (reader of magnetic strips) or any other equivalent reader adapted to detect said information when the component and the reading portion are approached one another (in contact or in proximity).

Further characteristics and advantages will better emerge from the following description in relation to some preferred but non-limiting embodiments of the invention.

SHORT DESCRIPTION OF THE DRAWINGS

Referring now to the enclosed figures several methods and corresponding apparatus will be described with reference, again by way of non limiting example, to replaceable components adopted in blood treatment apparatus.

The description will be made with reference to the figures of the accompanying drawings, also provided by way of non-limiting example, in which:

FIG. 1 is a block diagram showing the steps of the main flow of process executed by the control system of the apparatus of FIG. 14 when the reader of the apparatus of FIG. 14 reads information concerning a replaceable component or concerning a command;

FIG. 2 a block diagram showing the process followed after the steps of FIG. 1 by the control system of the apparatus of FIG. 14 when reading a concentrate related information via the reader;

Figure 1:
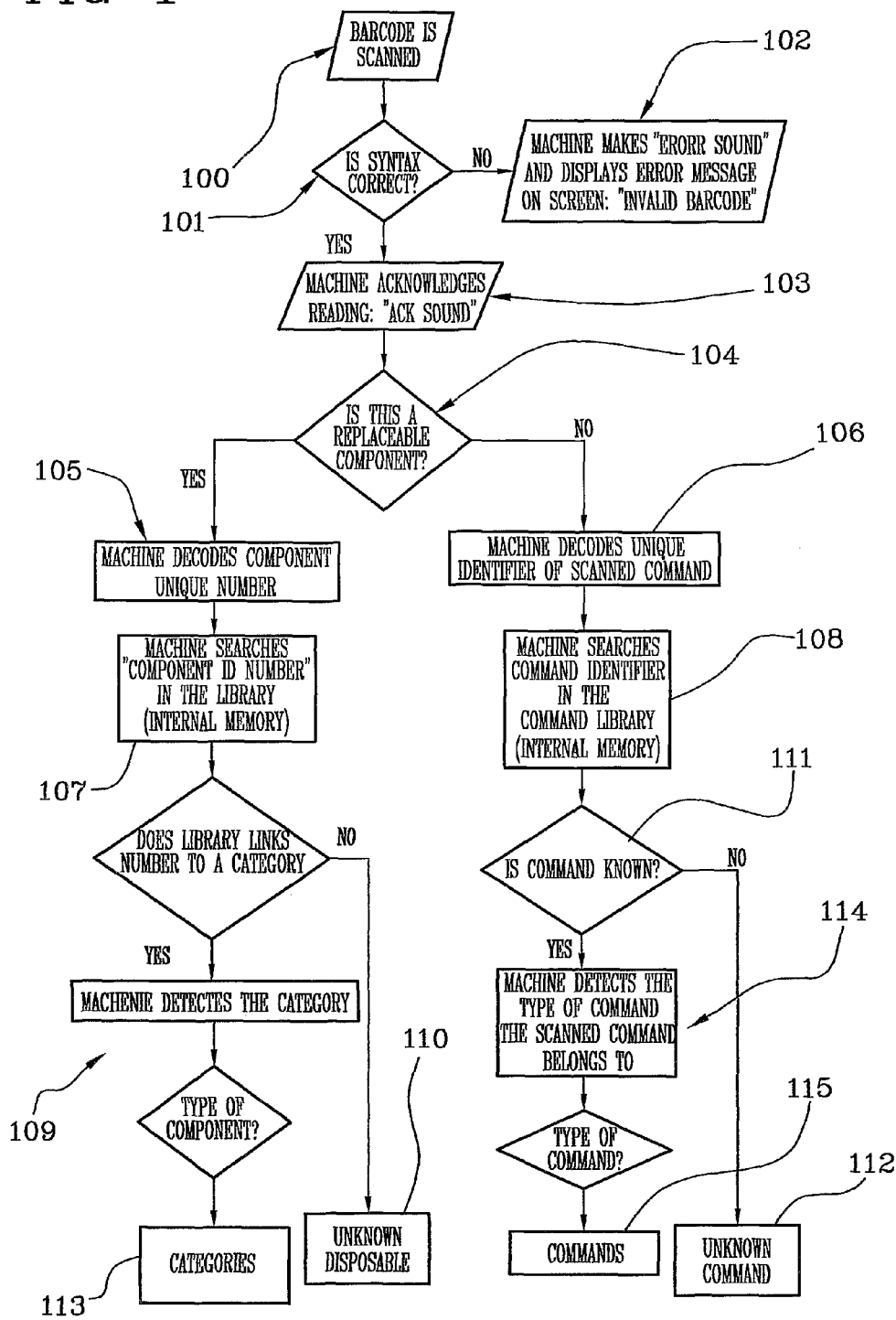
Figure 11:
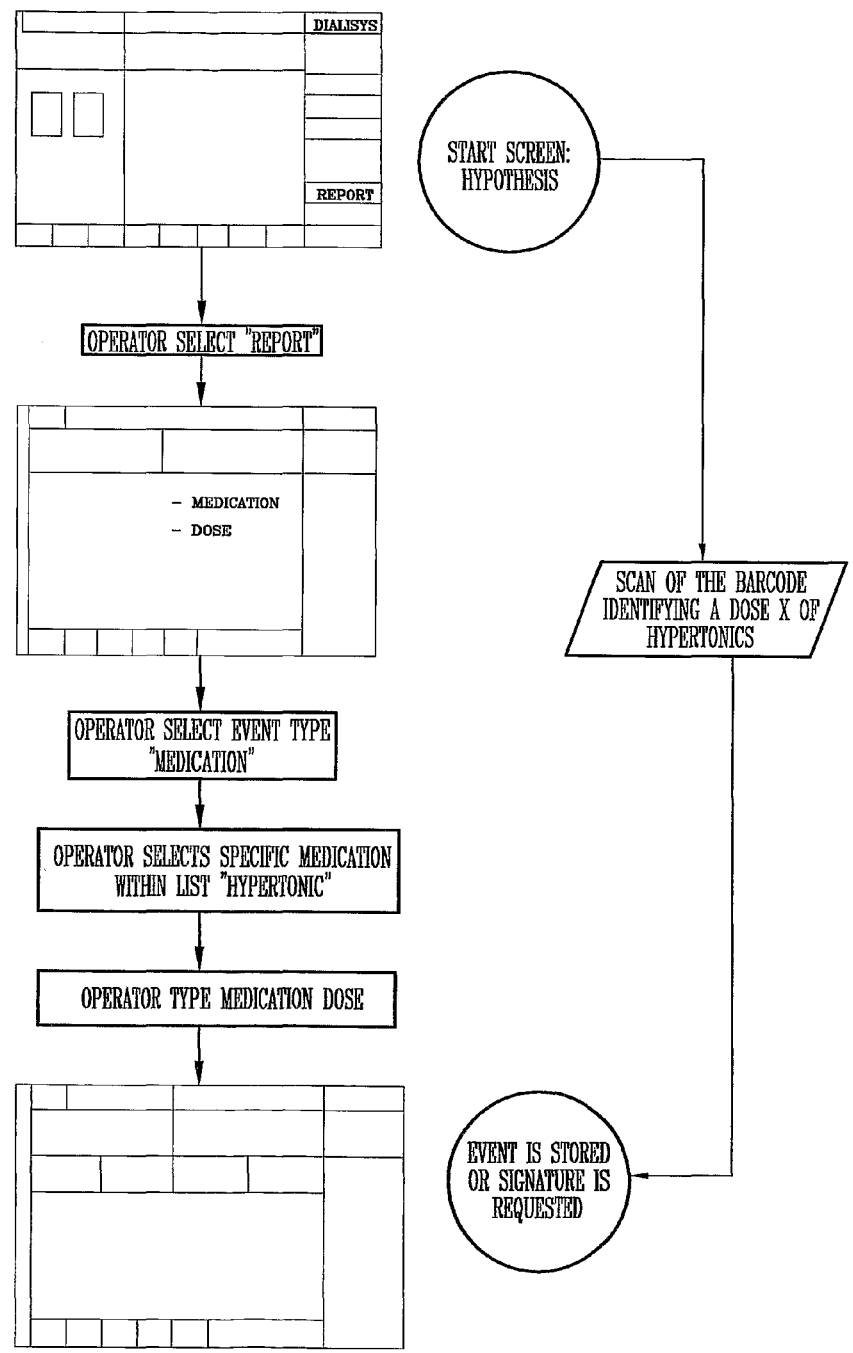
Figure 12:
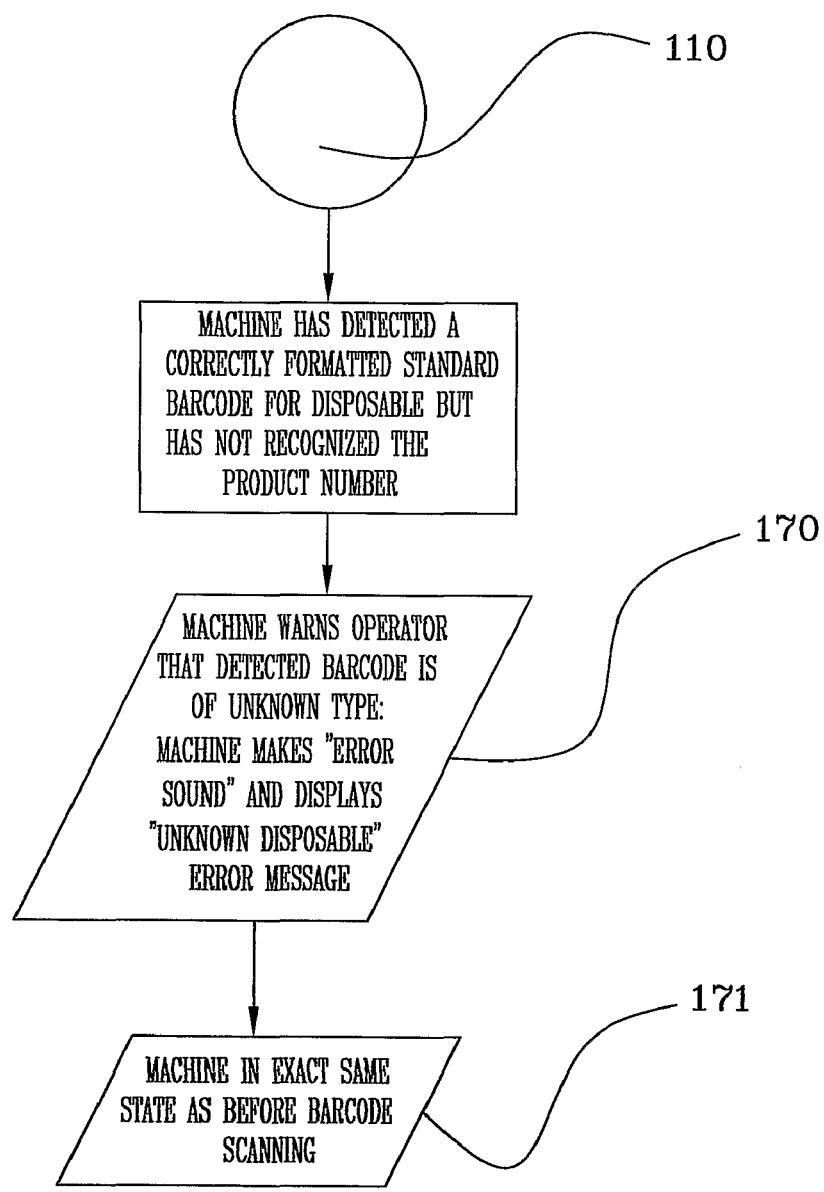
Figure 13:
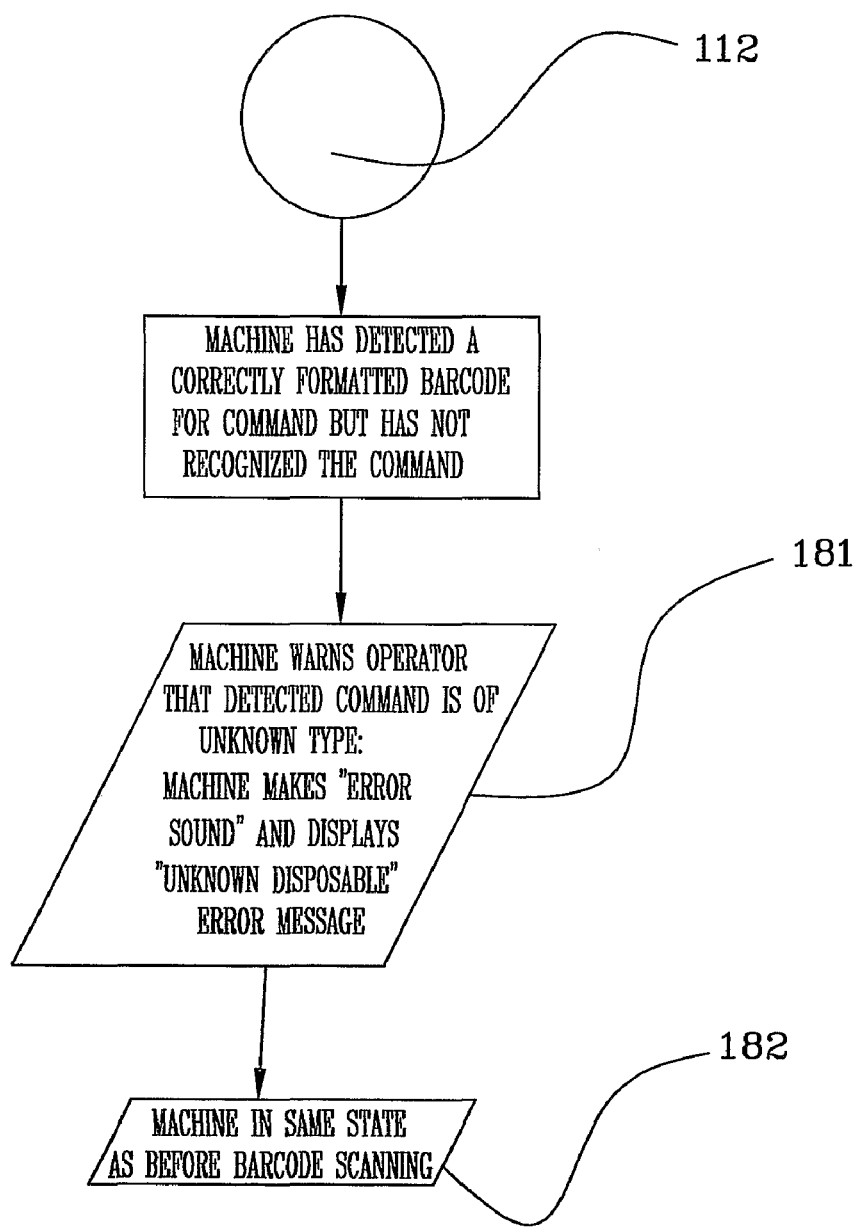
Figure 14:
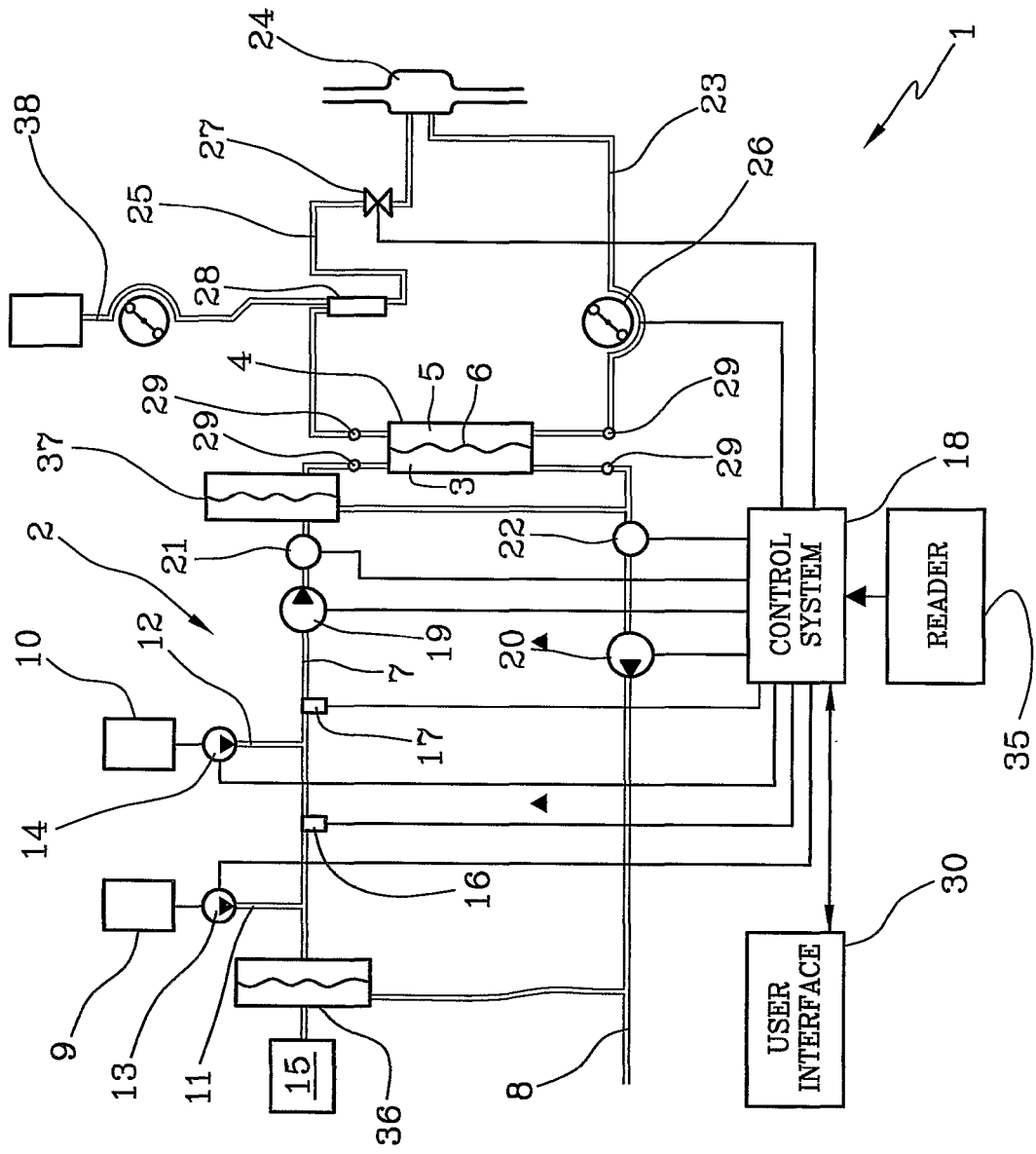
Figure 15:
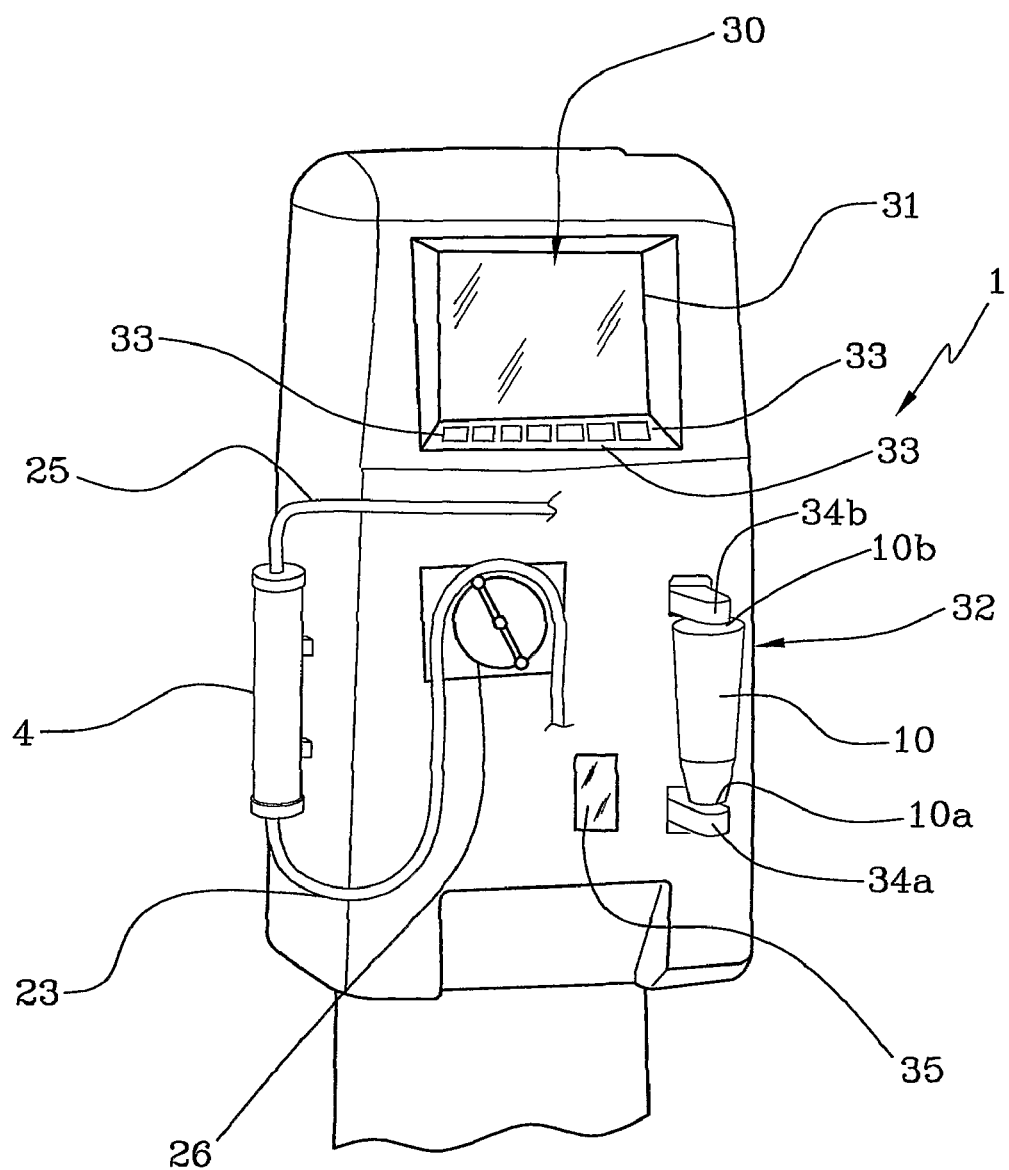

FIG. 11 a block diagram showing the steps performed by a user for inserting an event command when using the reader and when using the user interface 30, and FIGS. 12 and 13 are block diagrams showing the steps performed by the control system after the main flow of FIG. 1 if respectively the code is neither recognized as a known replaceable component nor as a known command;

FIG. 14 is a schematic view of the circuits of a blood treatment apparatus provided with a reader for reading information relating to replaceable components, according to the invention;

FIG. 15 is a schematic elevation of the blood treatment machine of FIG. 14.

DETAILED DESCRIPTION OF NON-LIMITING EMBODIMENTS

With reference to the enclosed figures, reference numeral 1 indicates a fluid processing medical apparatus according to an embodiment of the present invention.

The apparatus 1 of the non limiting embodiments herein described is an extracorporeal blood treatment machine for the treatment of pathologies such as kidney failure, liver failure, or congestive heart failure. While for sake of clarity and conciseness, the invention will be explained in detail with reference to an extracorporeal blood treatment machine, the invention could find application in other fluid processing apparatuses such as machines for processing whole blood or blood components coming from a donor or from a source (such as one or more containers), machines for blood oxygenation, machines for the cleaning or purification of water for medical use, machines for the preparation of medical fluids, machines for the delivery of medical fluids (infusion devices or drug administration machines), etcetera.

Going back to the embodiment of the attached figures, the apparatus 1 is an extracorporeal blood treatment machine able to perform one or more of the following extracorporeal blood treatments: ultrafiltration, dialysis, hemofiltration, and hemodiafiltration.

The apparatus 1 according to the embodiment of the drawings mainly comprises:

- A hydraulic circuit 2 for fresh treatment liquid, such as dialysis liquid, which in use is to be sent into a first chamber 3 of a blood treatment unit, 4 and/or infusion liquid, which in use is to be sent into the patient. The hydraulic circuit is responsible for bringing the treatment liquid to the treatment unit and/or directly to the patient with appropriate chemical and physical properties. The hydraulic circuit is also responsible for evacuating waste fluid from the blood treatment unit.
- A blood treatment unit 4 comprising at least a casing defining at least two chambers 3, 5 separated by a semipermeable membrane 6.
- Bloodlines 23, 25 connected to the second chamber of the blood treatment unit.
- A cabinet structure 32 housing the hydraulic circuit 2 and supporting, during treatment, the treatment unit 4 and the bloodlines 23, 25.
- A user interface 30 which is typically mounted on a front panel of the cabinet structure, but which could alternatively be in the form of an independent unit, separate from the cabinet.

The circuit 2 includes at least a supply conduit 7, bringing dialysis liquid to the first chamber inlet, and a waste conduit 8, receiving spent liquid exiting via an outlet of the first chamber. One or more concentrate sources of concentrates could be present. The concentrate sources could be designed to include containers for housing concentrated solutions or dry concentrates. In the enclosed embodiment containers 9, 10 deliver concentrated solutions, via respective lines 11, 12 and upon the action of respective concentrate pumps 13, 14, into the conduit 7 thereby properly mixing water coming from a source 15 with said concentrates and obtaining the dialysis liquid. In the machine of the enclosed embodiment one of the two containers, for instance container 10, is a dry concentrate cartridge. While not shown in the drawings, cartridge 10 is also connected, upstream line 12, to a source of water or of solution directly or indirectly coming from source 15. Conductivity or concentration sensors 16, 17 can be provided on conduit 7 downstream each respective concentrate line. Said sensors provide control signals to a control system 18 which is responsible to act on the concentrate pumps based on desired concentration settings and on said control signals. Sensors (not shown) detecting conductivity or concentration of electrolytes can also be present on the waste conduit 8. A pump 19 is generally operating on supply conduit 7 and a pump 20 on the waste conduit 8. Of course different alternative embodiments can be envisaged to bring dialysis liquid to the treatment unit with appropriate chemical and physical properties. For instance pre-prepared dialysis liquid bags or containers could be used, with no need of online preparation of liquid from concentrates and water.

Fluid balance sensors, for instance a first and a second flow-meter 21, 22, operating on the supply conduit 7 and on waste conduit 8 respectively, are used and are connected to the control system to provide signals necessary for regulating at least one of pumps 19, 20. Of course other fluid balance systems can be used: scales for instance or balance chambers or any other volumetric or mass or flow-rate based system available to the skilled man.

One or more ultrafilters could operate in the hydraulic circuit, upstream the treatment unit 4. For instance in the enclosed embodiment one ultrafilter 36 is present upstream concentrate line 11 and one ultrafilter 37 is placed downstream all concentrate lines 11 and 12.

The blood treatment unit 4 comprises at least a casing defining at least two chambers 3, 5 separated by a semipermeable membrane 6. The properties and type of membrane can vary depending upon the patient's needs and type of treatment to be executed: in particular the treatment unit could be an ultrafilter, an hemofilter, a dialyzer, an hemodiafilter, a plasmafilter etcetera.

The bloodlines 23, 25 connected to the second chamber of the blood treatment unit comprise an arterial branch 23, which in use serves to withdraw patient's blood to be treated, and a venous branch 25, which in uses serves to return treated blood to the patient.

The user interface 30 herein disclosed is connected with and part of the medical apparatus 1; however the user interface could be a self powered unit with wired or wireless connection to the control unit of the medical apparatus.

The user interface 30 of the embodiment shown includes a screen 31, for instance a touch screen, which allows interaction with the user interface, for instance selection of certain parameters, visualization, either in analogical or in digital form, of values of said parameters and display of other information; of course depending upon the case the user interface could include also buttons, knobs, or other hardware means 31 positioned off the screen and operable to introduce entries into the control system.

The activity of the user interface is determined by control system 18, which is connected to the user interface, is responsive to actions by a user on said user interface, and controls operations of the medical apparatus 1 by acting on a plurality of actuators (such as pumps 12, 13, 19, 20, 27, valve 27 and others) and by receiving signals from a plurality of sensors (such as for instance sensors 12, 13, 21, 22, 29 etc.).

The control system of presently shown embodiment includes a main control unit, connected to the user interface 30, and at least a memory connected to the main control unit. From a technical point of view the main control unit includes at least a microprocessor, while the above-mentioned memory can be in a single physical memory or in physically separated memory devices. Of course other alternative could be equivalently adopted, such as a control system partly or totally of analogical type.

In extracorporeal blood treatment apparatus, as the one just described, as well in other medical apparatus some components are replaceable, in the sense that they are replaced more or less frequently during the life of the apparatus, according to criteria which could vary depending upon the patient, the specific component, the market where the component is used, etcetera. By way of non limiting example, referring to a dialysis machine for chronic treatment as the one just described, the dialyzer, the blood tubing set, the access devices, the infusion lines and bags are replaced at the end of each treatment session or procedure. If a rinsing and/or priming procedure is activated using fresh liquid coming from a bag the empty bag is typically disposed of at the end of the procedure. The ultrafilters and concentrate containers used for the preparation of treatment liquid can be changed at the end of each treatment session, or after a number of sessions, or after a number of working hours.

In conclusion, with reference to the blood treatment apparatus just described, a number of components are replaceable components: the concentrate containers 10, 11 (which can be in the form of deformable bags or rigid containers, containing concentrated either in liquid or in solid form), the bloodlines 23, 25, the blood treatment unit 4, the ultrafilters 36, 37 in the dialysis preparation circuit, any infusion lines 38, the bags or other containers for the injection of fluids into the blood circuit or into the blood lines, the access devices (needles, catheters, or the like).

As can be easily understood, the apparatus of the type described can host and use a plurality of components of the same category: for instance the same blood treatment apparatus can alternatively use a number of different blood treatment units, or a number of alternative bloodlines, or a number of alternative concentrate containers etcetera. Typically before each treatment, an operator selects the needles, bloodlines, bags, dialyzer or other blood treatment unit, as well as other replaceable components ideal for that specific treatment. The apparatus has engaging means differentiated per type of component: for instance the ultrafilters located in the fluid preparation section of the hydraulic circuit present connectors positioned and shaped so that they cannot be engaged in place of the dialyzer; each component of the same category presents respective mechanical connections to the apparatus different from those of the components of other categories, so that each replaceable component fits with the respective connections on the machine and setup mistakes on the part of the operator are minimized.

More precisely, the means for engaging replaceable components of different categories comprises a plurality of different types of engaging means, each type of engaging means being designed for engaging, in a respective operating area, respective components of one corresponding category only. Practically all concentrate containers of the same category (for instance all bicarbonate containers) have identical connectors and engage with corresponding ports suitably shaped on the apparatus: the cartridge 10 has for instance two opposed connectors or ports 10a, 10b receivable in corresponding ports or connectors 34a, 34b of the apparatus 1. Analogously all bloodlines are designed to engage corresponding seats on the apparatus, seats which are not suitable for hosting the concentrate containers or other components. In the same manner all blood treatment units (hemofilters, dialyzers, hemodiafilters, etcetera) form another category and have connector or ports designed to couple with a corresponding engaging means (which can include tubular ports and or counter-connectors other support mechanisms to hold in place the unit 4) on the support structure of the apparatus.

Before using the described apparatus, a user should prepare it for the specific treatment to be delivered. The user should install all replaceable components: put in place the bloodlines, the treatment unit, the various concentrate containers, substitute the ultrafilters if necessary, install all necessary bags and infusion lines. Then a priming process is started to clean, rinse and to remove air from all components which are expected to enter in contact with blood or with treatment liquid.

In view of this situation it is fundamental when setting the machine to inform the machine about the specific components that have been mounted as the procedures or treatments that the machine can deliver are in general related to the components used. In order to enter setup information, the user can enter data of any kind relying on the user interface: for instance, prescription data, treatment selection information, and of course data relating to the components installed on the machine.

As it will be explained in detail the user can navigate through the various levels or menus of the user interface 30 and select or enter the information corresponding to each replaceable component installed on the machine.

In order to facilitate the data entry process, a reader 35 is provided operatively connected with the control system 18 and having a reading portion for reading information concerning the components. Each replaceable component is associated to a respective information; the information is borne by the respective component (i.e. on a label or directly on the component) or by the respective component packaging or by a card or other support; the nature of the reader is such that to read the information it is necessary approaching to one another the component and the reading portion (depending upon the nature of the reader, which could be an optical reader such as a linear or bi-dimensional bar code reader, an radio based reader such as RFID reader, a mechanical reader, or a reader of other nature, the user will need to approach more or less the information support to the reading portion or even put reader and information support into contact). In accordance with one aspect of the invention the information carrier and the reading portion should either be put into reciprocal contact or relatively approached at a distance in the range of 30 cm or less.

The reader can be fixed to the apparatus support structure or be in the form of a movable reader connected to the apparatus control unit via wires or wireless.

In any case the reading portion of the reader is always operating in a position distinct and spaced from said operating areas where the replaceable components are expected to operate in use conditions. In this way, the reading portion is accessible for reading the information irrespective of the components being engaged or not to the apparatus.

Going now to the specific embodiments of the attached figures, FIG. 1 discloses in form of block diagram the steps followed by the control system. As mentioned the control system can include a microprocessor based control unit which is suitably programmed to execute the steps here below disclosed. Alternatively the control system can be an analogical system which is designed to carry out the steps as below described. In any case the control system by way of intrinsic design or by way of a suitable program includes means for performing the steps below described.

While it will not be repeated for each step in below description it is intended that the control system is programmed for, or includes means for, performing each one of below steps. These means included in the control systems can be suitably designed analogical circuit portions or programmed digital circuits of a control processing unit.

Referring to FIG. 1 the control system receives the scanned code, for instance a barcode, from the reader 1 (step 100). The control system communicating with the reader is programmed for receiving the information concerning the components: in practice, every time a new component is approached to the reader (or the reader to support bearing the component information) sufficiently for the reader to read information concerning a component to be installed on the apparatus, then said read out information is transferred to the control system 18. The control system then verifies if the syntax of the scanned code satisfies predefined criteria (step 101) and in the negative generates and error signal (which can be audible and/or displayed on the screen 31), as per step 102.

The control system can also generate an acknowledgement message and/or sound, when on the other hand the barcode syntax is correct (step 103).

Then the control system verifies if the scanned code corresponds to a code of replaceable component (step 104) and in the affirmative decodes the product number (step 105), for instance by comparing it with a list of numbers stored in the control system memory (step 107).

In the negative, the control system decodes the command number (step 106), for instance by comparing it with a list of numbers stored in the control system memory (step 108). In practice, depending as to whether the code corresponds to a component or to a command the control system follows one of the two branches of the diagram of FIG. 1.

If the control system has detected a code of a component, then the identity of said component is searched in the library present in the control system memory and first the category of the component is identified (step 109) and a corresponding procedure initiated (step 113); if a component category, is not identified a corresponding audible and/or displayable signal is generated (step 110).

If the control system detects a command code, in step 111 the control system verifies if the command is known or not. In the latter case a audible and/or displayable signal is generated (step 112). If the command code is recognized as one of the known commands, the type of command is detected (step 114) and a corresponding procedure initiated (step 115).

Figure 2:
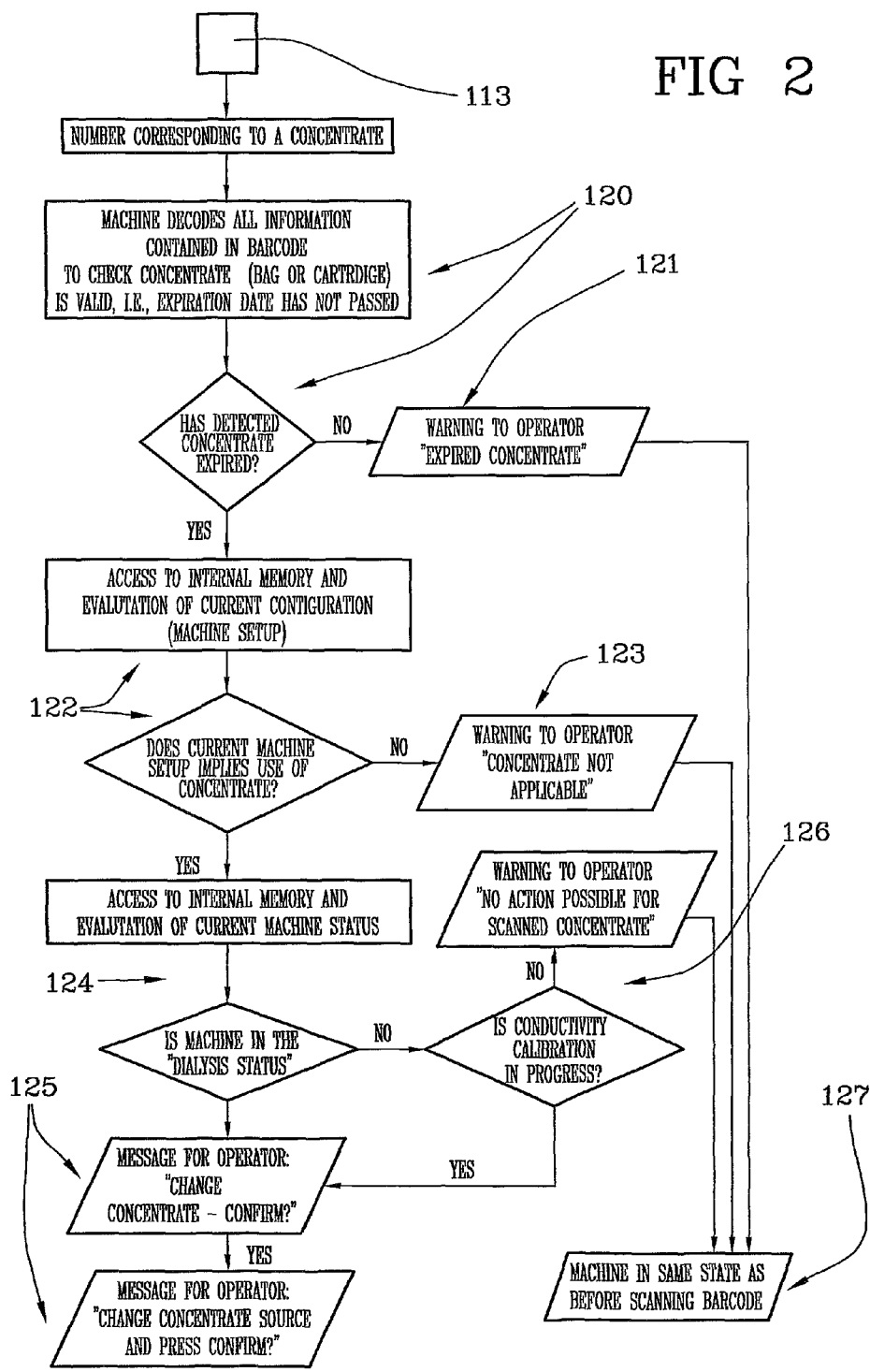
Figure 4:
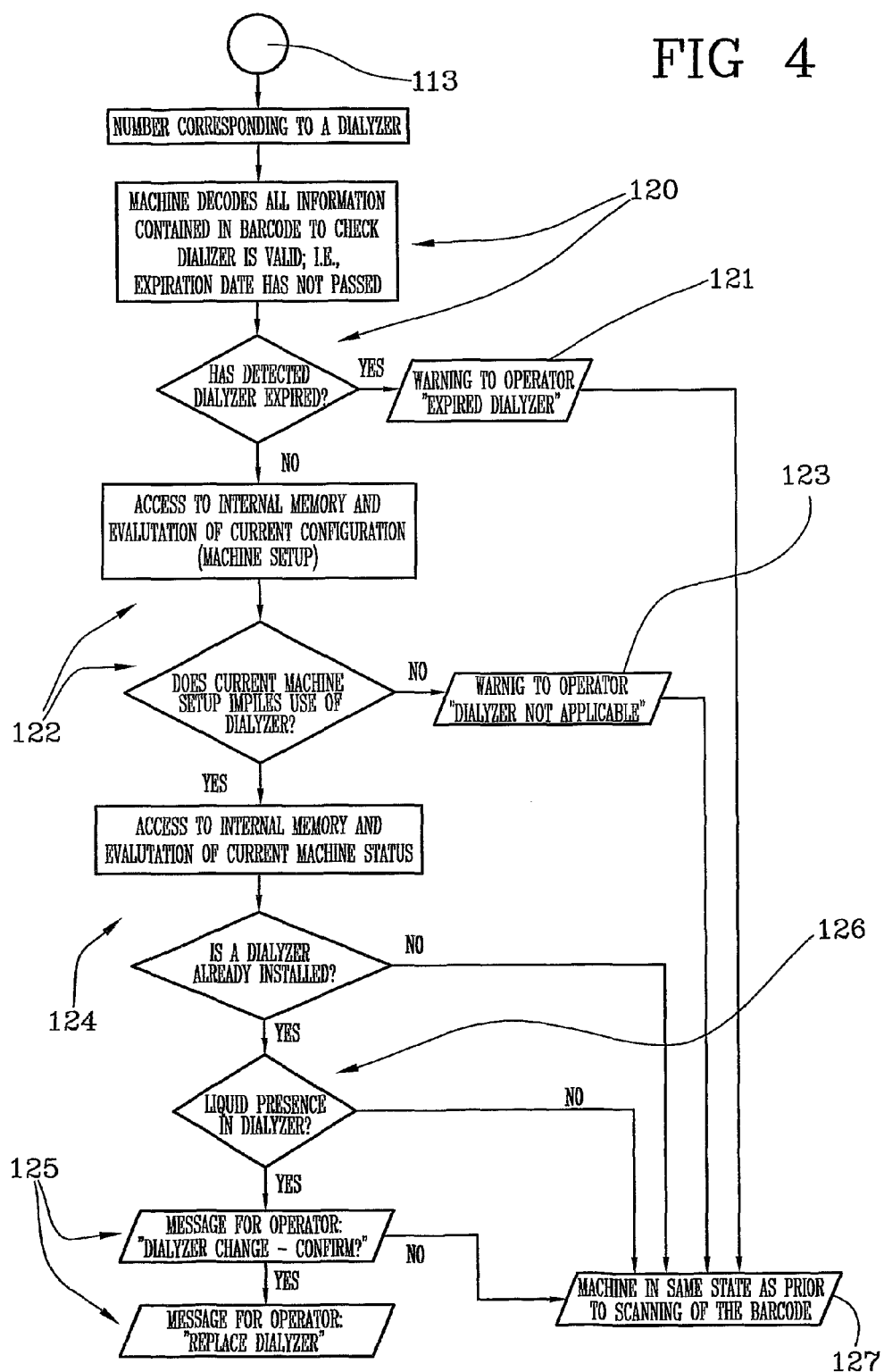
FIGS. 4 and 5 show the process followed after the main flow of FIG. 1 by the control unit of the apparatus of FIG. 14 when respectively a dialyzer or a bloodlines code.
Figure 5:
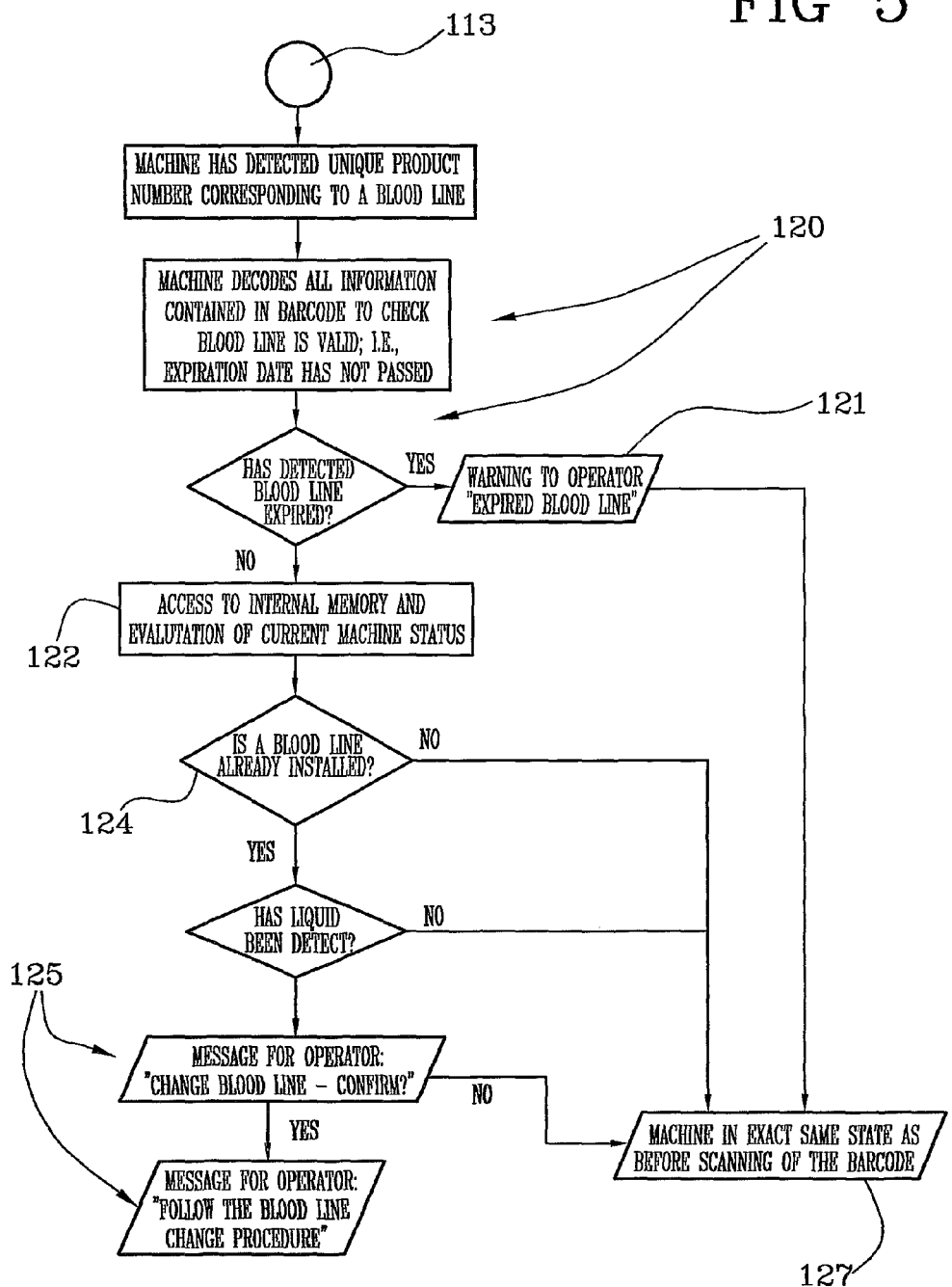

In case for instance the control system has detected a component code corresponding to a concentrate, then the procedure and steps of FIG. 2 is followed. If the control system has detected a component code corresponding to a dialyzer, then the procedure and steps of FIG. 4 is followed. If the control system has detected a component code corresponding to a bloodline, then the procedure and steps of FIG. 5 is followed. Of course component of other categories could be encompassed with slightly different procedures followed by the control system depending upon the category of the component.

In FIG. 2, after the step 113, the control system verifies that the number is that of a concentrate, checks expiration date or other validity parameters (step 120), and warns accordingly the operator through audible and/or visual signals (step 121). The control system verifies then if the machine setup or configuration requires the detected type of concentrate (step 122) and in the negative warns accordingly the operator through audible and/or visual signals (step 123)

The control system also verifies the status of the apparatus in order to detect if the new component the code of which has been just read is of the same category of a component (same dry concentrate for instance) already installed on the machine (step 124). In the affirmative the control unit is also programmed for signaling that a component of the same category is already installed on the apparatus. If the control unit verifies that a component of the same category as the one read by the reader, then the control unit is programmed for requesting for confirmation to substitute the installed component with the new component (step 125). In case a conductivity calibration procedure is ongoing the control system informs that it is not possible to take any action for the scanned concentrate (step 126). In case the concentrate is not valid, or not applicable in view of the apparatus selected treatment, or if a calibration or other momentary procedure preventing substitution of the specific component is ongoing, then the control system returns to a condition where it is ready to receive a new bar code reading (step 127).

FIG. 4 and FIG. 5 flow diagrams are very similar to the above described diagram and procedure of FIG. 2, so the steps 120, 121, 122, 123 executed by the control system will not be described again as the only difference is that in FIG. 4 a dialyzer code is detected and in FIG. 5 a bloodlines code is detected. As to FIG. 4 it is however to be noted that in case a dialyzer code is detected the control system verifies the status of the treatment procedure and if a dialyzer is already installed (step 124). Then it also verified if priming of the dialyzer currently installed is still running and if it has been completed or not (step 126). Steps 125 and 127 are similar again to those of FIG. 2 for the concentrate code. As to FIG. 5, after step 122 the control system verifies if a bloodline is already installed on the machine and also if blood has been already sensed by use for instance of a sensor (a sensor associated with the bloodline and able to detect blood presence such as an optical sensor or a conductivity sensor or an electromagnetic sensor or a capacity sensor can be alternatively used. The sensor is in communication with the control system). Steps 125 and 127 are similar again to those of FIG. 2 for the concentrate code.

Figure 6:
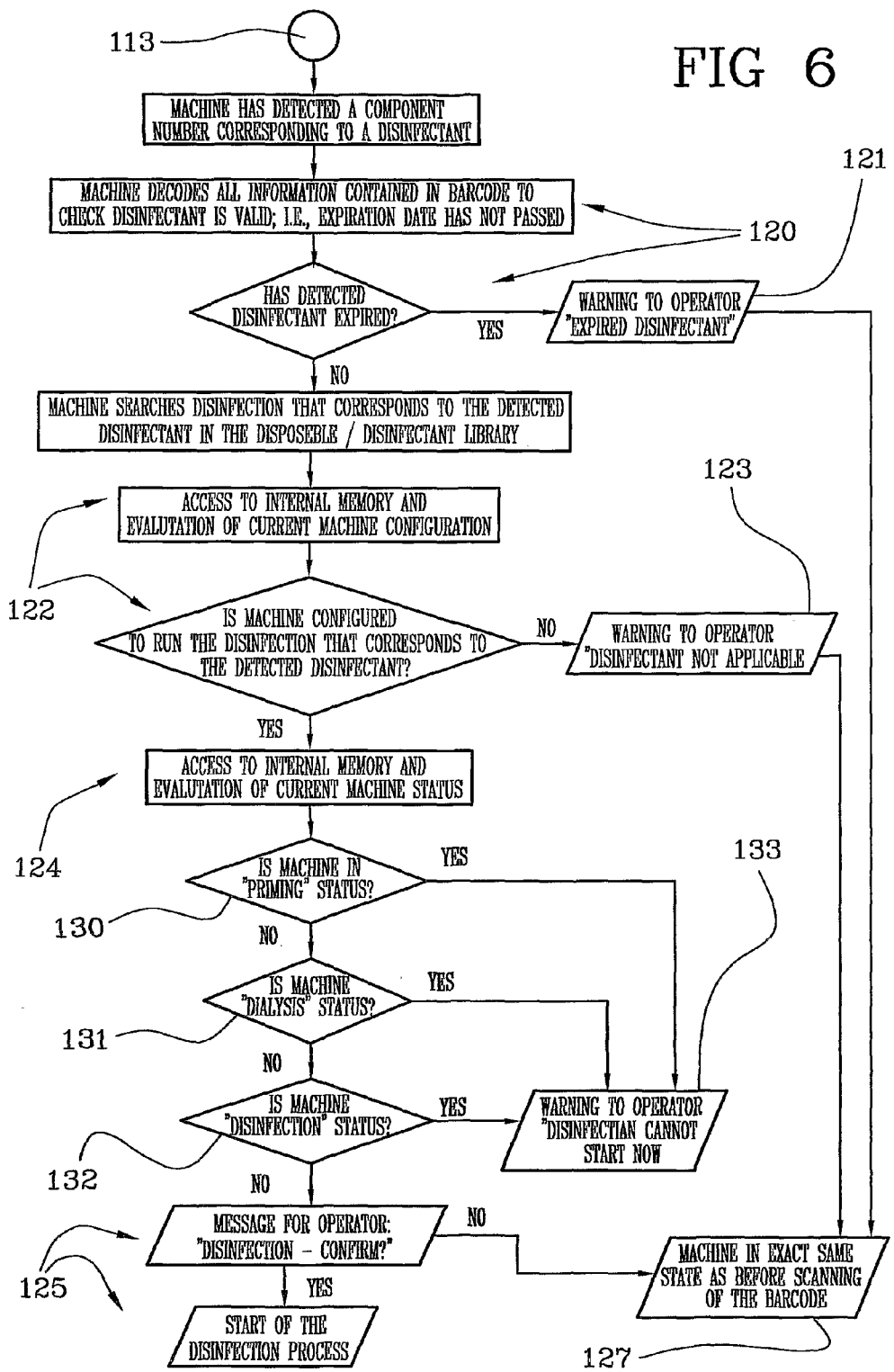
FIG. 6 is a block diagram showing the process followed control system 18, after the main flow steps of FIG. 1, when a disinfection procedure is initiated upon a code of a disinfectant is read.

FIG. 6 diagram shows the procedure followed by the control system when a the code of a disinfectant replaceable component is detected. FIG. 6 flow diagram is very similar to the above described diagram and procedure of FIG. 2, so the steps 120, 121, 122, 123 executed by the control system will not be described again as the only difference is that in FIG. 6 a disinfectant code is detected. In FIG. 6 flow, after step 122 the step 124 of verifying the machine status includes verifying if the blood treatment apparatus 1 is in one of the following operating conditions:

priming status (step 130), i.e. a status where lines are washed and rinsed before the treatment.
dialysis status (step 131), i.e. the true blood treatment,
disinfection status (step 132), i.e. disinfection of the circuit 2 after treatment.

If the apparatus is in one of the above conditions, then a step 133 is executed where the control systems generates a visible and/or audible signal warning the operator that a disinfection procedure of the blood treatment apparatus cannot be started.

Steps 125 and 127 of FIG. 6 are similar to those of FIG. 2, but for the fact that a disinfection confirmation is required and that after confirmation a disinfection procedure will start.

Figure 8:
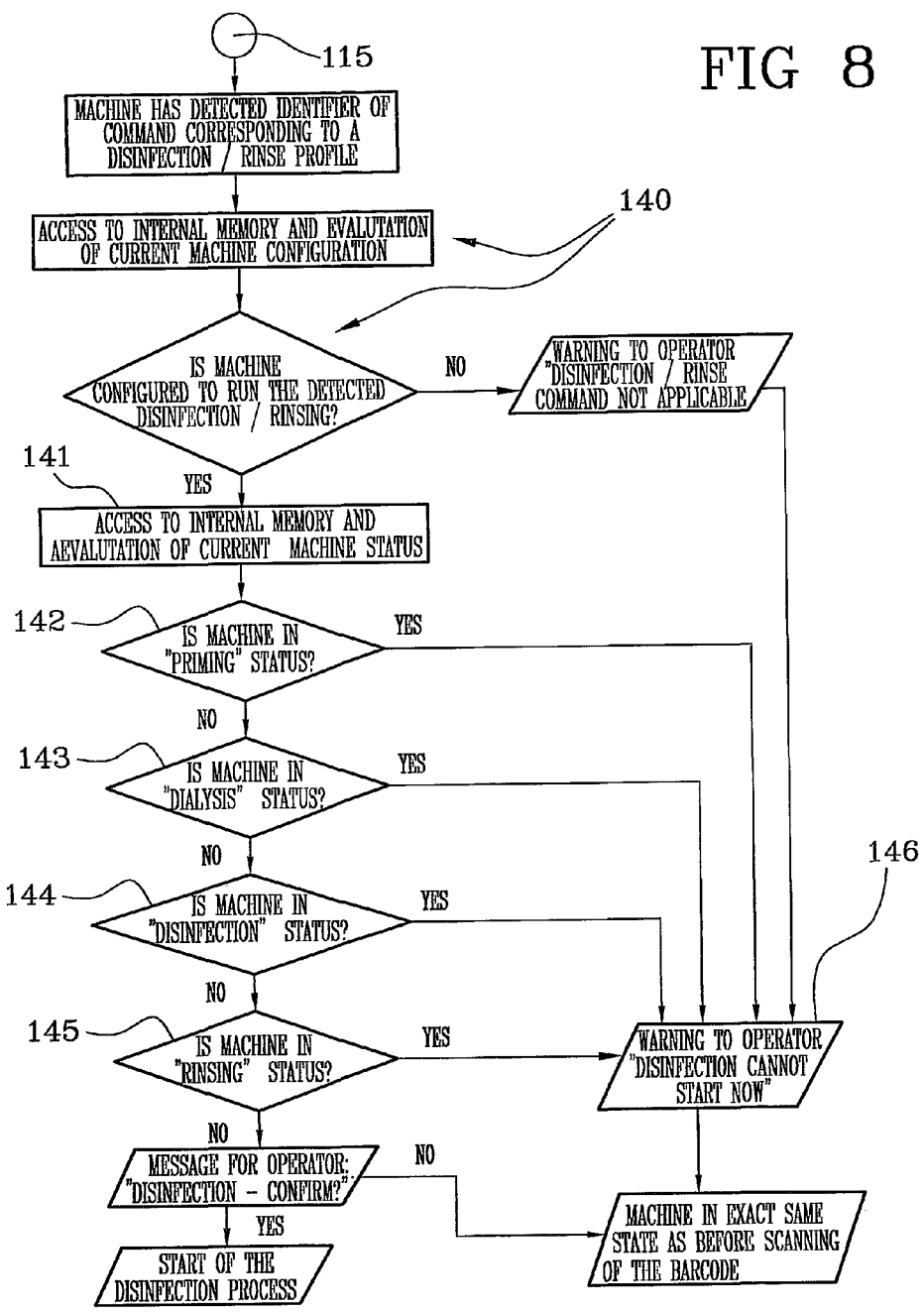
FIGS. 8-10 show the procedure followed by the control system 18 of apparatus of the invention when using the reader for entering commands, such as by way of non limiting examples: DISINFECTION, RINSE or SERVICE COMMAND.

FIG. 8 diagram shows the procedure followed by the control system when a code of a command corresponding to a disinfection rinse profile is detected a disinfectant replaceable component is detected. The control system then verifies if the configuration of the machine is adapted to run the command (step 140). In the affirmative the control system verifies if the machine status (step 141), which includes verifying if the blood treatment apparatus 1 is in one of the following operating conditions:

priming status (step 142), i.e. a status where lines are washed before the treatment.
dialysis status (step 143), i.e. the true blood treatment,
disinfection status (step 144), i.e. disinfection of the circuit 2 after treatment,
rinsing status (step 145), i.e. when the lines are rinsed after a treatment.

If the apparatus is in one of the above conditions, then a step 146 is executed where the control systems generates a visible and/or audible signal warning the operator that a disinfection procedure of the blood treatment apparatus cannot be started.

Steps 125 and 127 of FIG. 8 are similar to those of FIG. 6.

Figure 9:
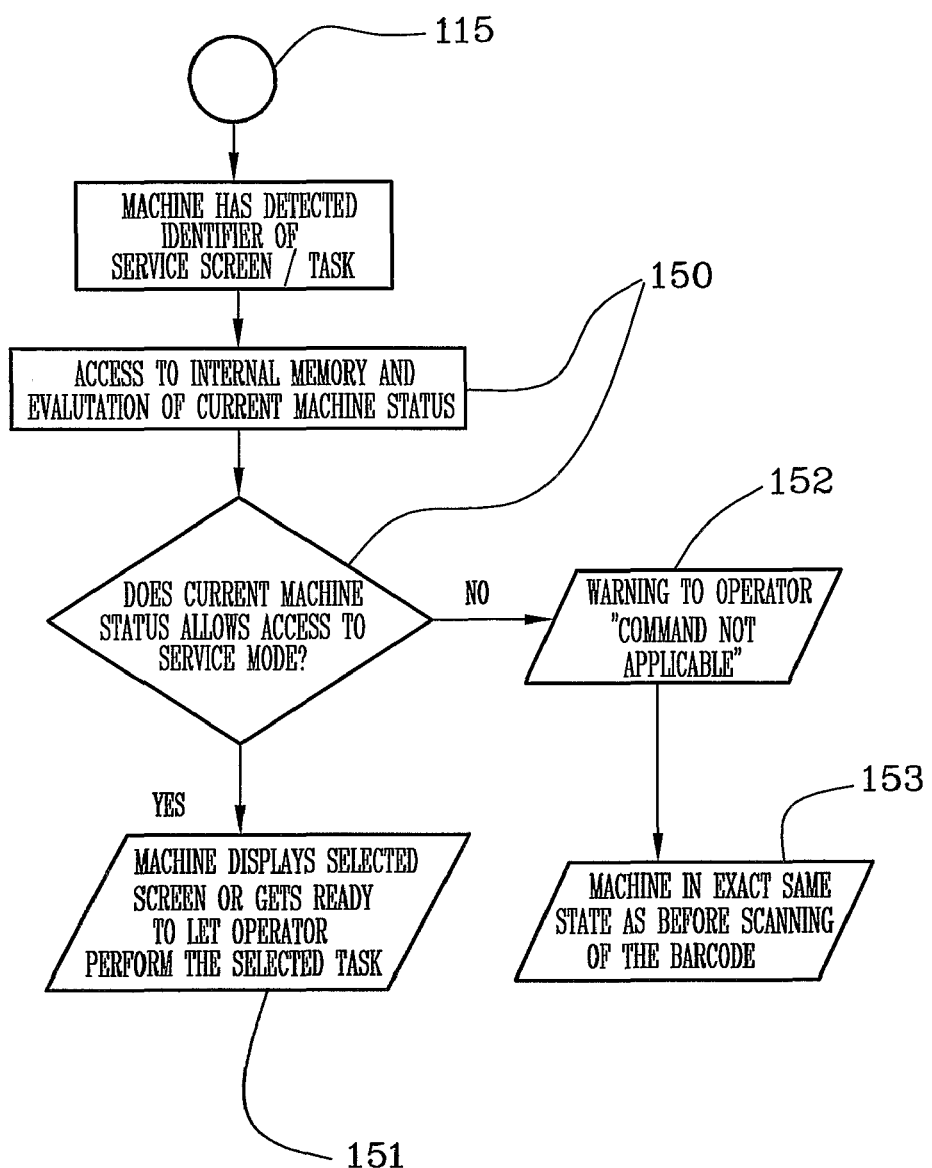

FIG. 9 diagram shows the procedure followed by the control system when a code of a command corresponding to a request to go to a service screen or to perform a task is detected. The control system then verifies if the status of the machine is adapted to allow the command, i.e. to access to the status screen (step 150). In the affirmative the control system loads on the user interface screen 31 the service screen and allows the operator to interact with it (step 151). If the command is a task, after step 150 the control system will let the operator to perform the task in question. If the check of step 150 is negative, then control systems generates a visible and/or audible signal warning the operator that the command is not applicable (step 152) and then the control system returns to a condition where it is ready to receive a new bar code reading (step 127).

Figure 10:
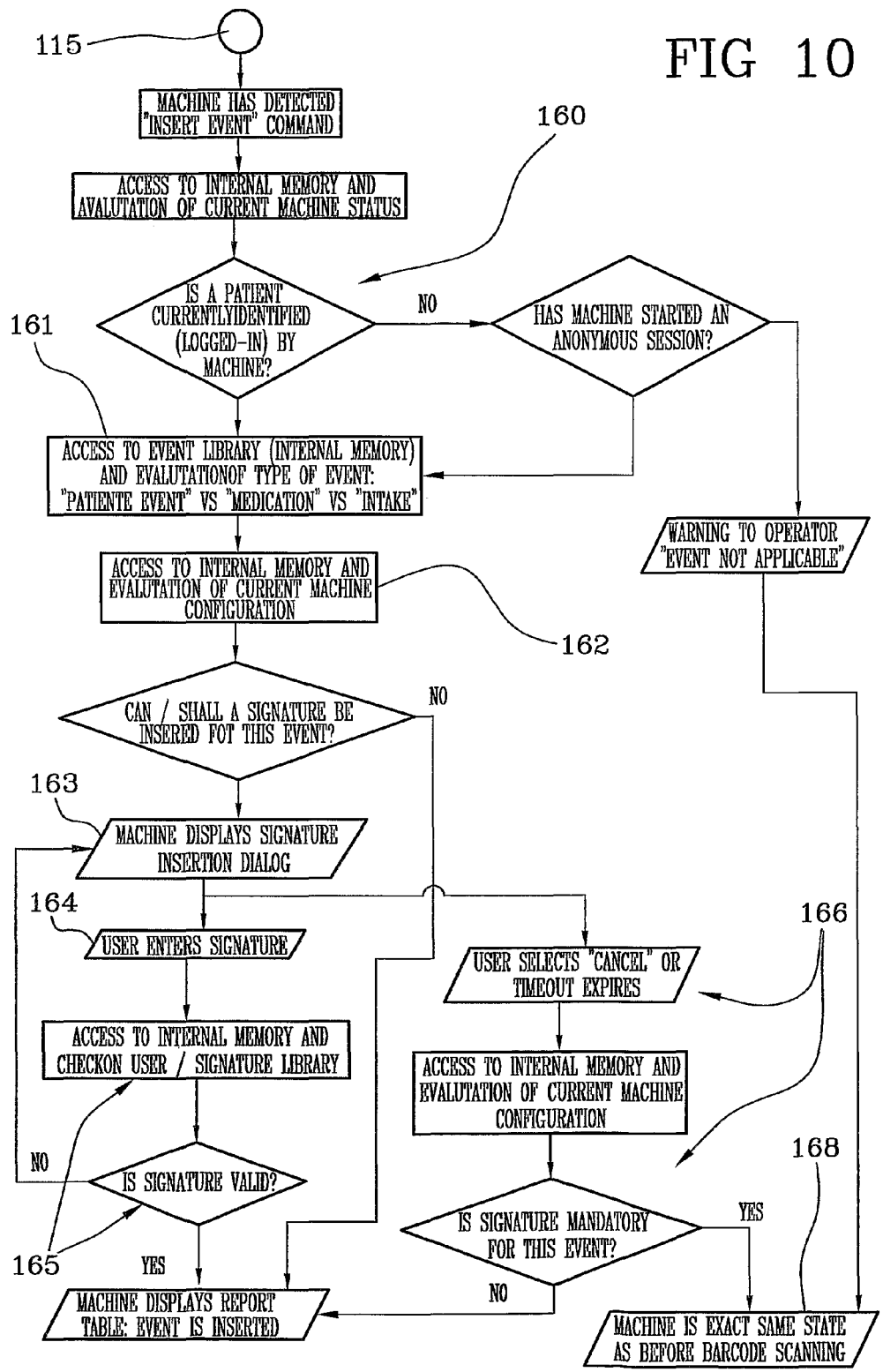

FIG. 10 diagram shows the procedure followed by the control system when a code of a command corresponding to an event that needs to be inserted is detected (events can be for instance: a medication given to the patient, a patient problem that has been detected and so on). The control system then verifies if the status of the machine is adapted to receive the event command (step 160). Then the control system compares the event command with a list of events stored in a library (step 161) and also checks the apparatus configuration (step 162). The control system then verifies if for the entered event command a signature is necessary or not (step 163). In the affirmative the signature is allowed to be entered (step 164) via an appropriate means (a touch screen portion can be used) and validated by comparing it with a signatures library (step 165). In case of no validation the control system returns to step 163. In case the signature is not mandatory (steps 166) or if the signature has been validated the control system moves to step 167 where the event is recorded and inserted in a report table. In case a signature has not been inserted, but it is required for the event, then the control system returns to a condition where it is ready to receive a new bar code reading (step 168).

FIG. 12 diagram shows the procedure followed by the control system when a correctly formatted unknown code of a replaceable component is read. The control systems generates a visible and/or audible signal warning the operator that the code is unknown (step 171) and then the control system returns to a condition where it is ready to receive a new bar code reading (step 172).

FIG. 13 diagram shows the procedure followed by the control system when a correctly formatted unknown code of a command is read. The control systems generates a visible and/or audible signal warning the operator that the code is unknown (step 181) and then the control system returns to a condition where it is ready to receive a new bar code reading (step 182).

Figure 3:
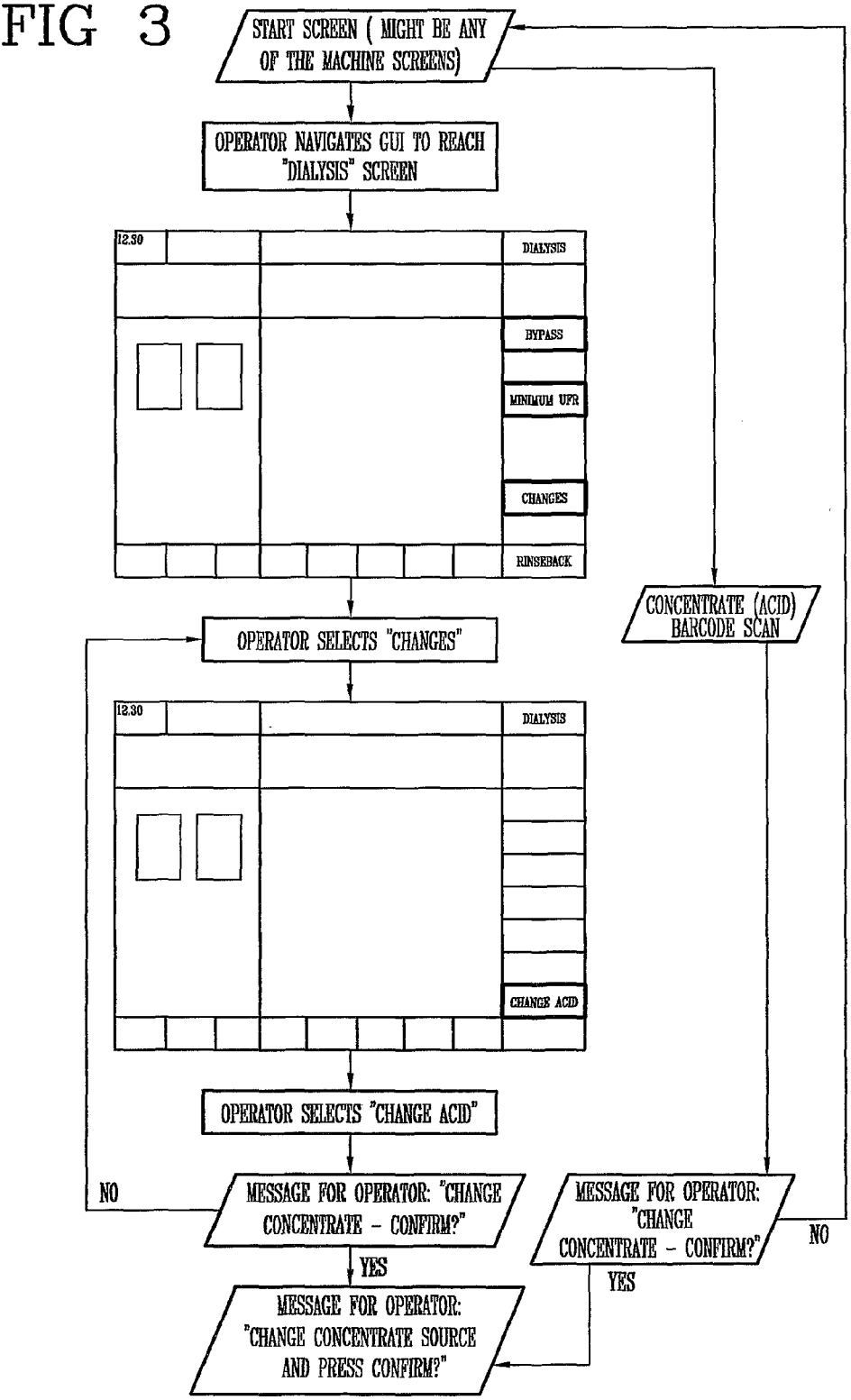
FIG. 3 is a block diagram showing the steps performed by a user for changing a concentrate container using the apparatus of FIGS. 1, 2 and 14.
Figure 7:
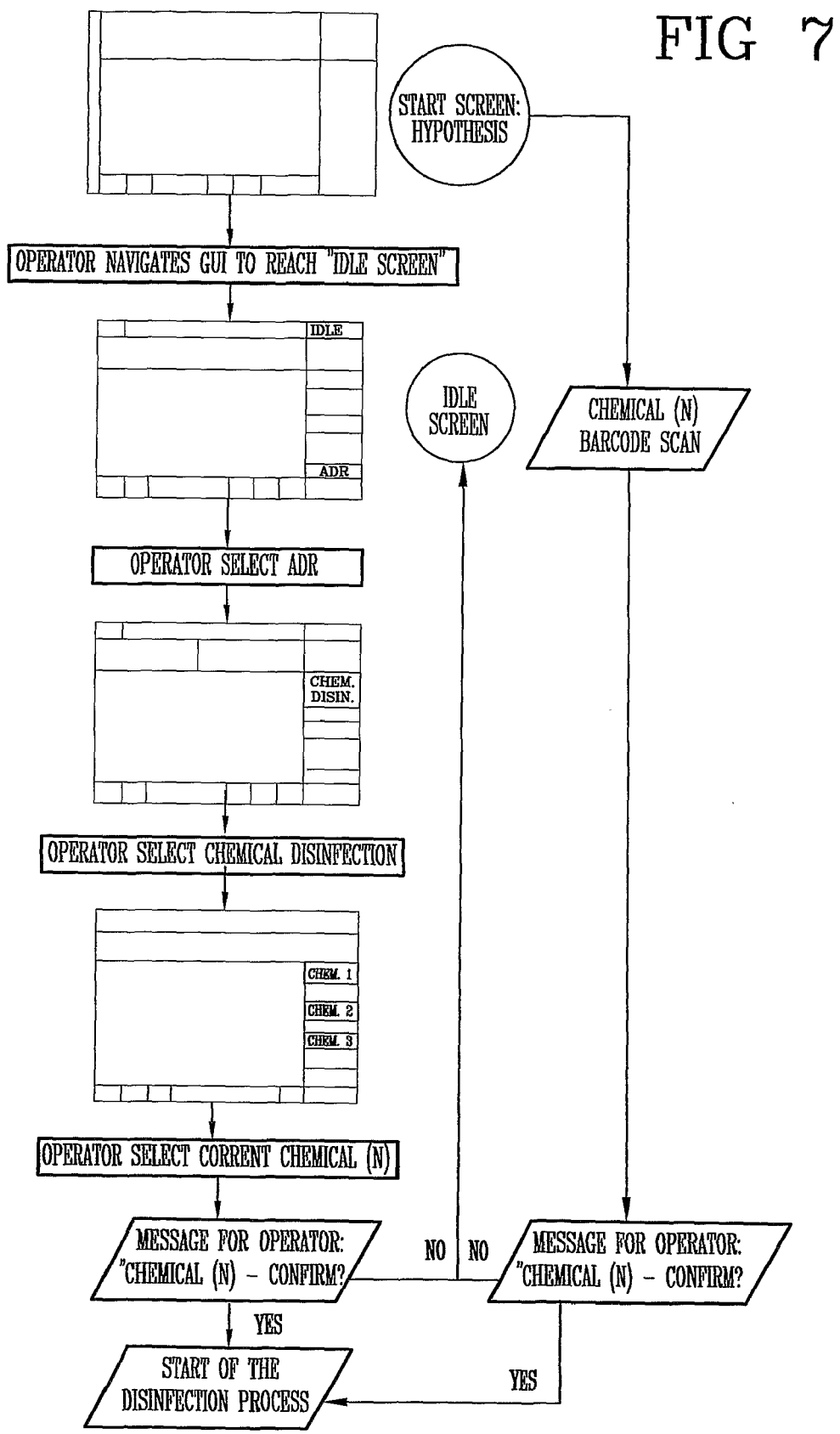
FIG. 7 is a block diagram showing the steps performed by a user for initiating a disinfection procedure.

Going now to FIGS. 3, 7 and 11 comparatively showing the steps performed by a user when using the reader (right side of each figure) and when using the user interface 30 (left side), it is clear how advantageous id the reader for entering commands and components identities. Of course the presence of the user interface which also allows to manually enter the same commands and information in the control system gives redundancy and consequently high reliability.

The above steps subsequent to reading of a code can be basically repeated by the control system every time the reader reads information concerning a component to be installed on the apparatus or a command to be executed.

The above apparatus and method have been described assuming that the reading portion is always active, i.e. in a status where it is able to read information. While this could be the case, it is also alternatively possible to have activation and de-activation of the reader and of the reading portion depending upon the following circumstances.

In particular, the control system of the apparatus 1 could be programmed for receiving a information concerning a fluid treatment procedure selected by a user (by acting on the user interface for instance), and then verifying if the selected fluid treatment procedure requires or not use of the reading portion. For instance in case of a blood treatment machine after set up of the machine the machine can start the extracorporeal blood treatment. During such a treatment it is normally not necessary to enter data using the reader and this latter can be conveniently turned off. The de-activation of the reading portion, when the selected treatment procedure does not require use of the reading portion, can be automatic (i.e. upon detection of the selection or of the start of the specific procedure) or commanded by the user acting on the user interface (which can have an appropriate key or dedicated area). The control system can also be programmed for de-activating said reading portion, when the reading portion reads no information during a prefixed timeout period.

The control system can also be programmed for verifying if the selected fluid treatment procedure requires or not use of the reading portion and for activating said reading portion, when the selected treatment procedure does require use of the reading portion.

In accordance with one embodiment the control system is programmed for activating said reading portion, when the apparatus is turned on.

With the reference to the example of the enclosed drawings where the apparatus 1 is an extracorporeal treatment machine, the control system can be programmed—and thereby includes means—for executing one or more of the following steps of detecting that:
  a) a setup procedure has been selected or initiated (which could include one or more steps of setting a prescription, preparing the machine for treatment by engaging any replaceable components with the machine, etcetera),
  b) a blood treatment session has been initiated or that a command to initiate a blood treatment procedure has been entered through the user interface,
  c) a blood treatment session has been concluded or that a command to stop a blood treatment procedure has been entered through the user interface,
  d) a rinse back procedure has been initiated or that a command to initiate a rinse back procedure has been entered through the user interface.

The control system can be programmed—and thereby define means—for turning the reader on upon detection of a) or of c) or of d) and for turning the reader off, upon detection of b).

The medical apparatus 1 above described represents a non-limiting example, which the present invention can be applied to. The apparatus can of course include other components, which are not herein disclosed, as they are not relevant for the purpose of the understanding of present invention.

For instance when verifying the compliance of a component with a selected treatment procedure, this can be done in practice by relying on appropriate sensors of presence, such as mechanical switches or electromagnetic sensors or optical sensors or equivalents thereof (operative in correspondence of the operating areas of the various components), or by means of indirect tests on the fluids interested or affected by the presence of said components (for instance if a concentrate container is present, then conductivity in the treatment liquid is affected, if a dialyzer is present pressures in several parts of the circuit 2 and bloodlines are affected, if an ultrafilter is present again pressure sensing can be used).

The invention claimed is:

1. Method for setting-up a fluid processing medical apparatus, the apparatus being of the type comprising:
   a support structure for receiving a plurality of replaceable components of different categories in correspondence of respective operating areas of said apparatus,
   at least a user interface for enabling setting of a plurality of parameters pertinent to operation of said apparatus or pertinent to a process to be performed by said apparatus, the user interface including at least a screen,
the method comprising the following steps:
   providing a reader having a reading portion for reading information concerning the components, the reading portion being distinct and spaced from said operating areas and accessible for reading the information irrespective of the components being engaged or not with apparatus,
   reading the information of a new component to be installed on the apparatus by relatively approaching the reading portion to a carrier of said new component information,
   coupling the new component with the apparatus in correspondence of a respective of said operating areas, the component when coupled leaving the reading portion accessible for reading the information,
   the method further comprising the steps of:
   selecting a desired treatment procedure,
   checking if the new component fits with the selected treatment procedure,
   signaling if the new component does not fit with the selected treatment procedure.

2. Method according to claim 1, wherein after the reading step it is provided a step of verifying if the new component is of the same category of a component already installed on the apparatus.

3. Method according to claim 2, comprising the step of signaling that a component of the same category is already installed on the apparatus.

4. Method according to claim 3, herein after the signaling step, the following steps are provided:
   requesting for confirmation to substitute the installed component with the new component,
   initiating a procedure for substitution of the installed component with the new component.

5. Method according to claim 4, wherein the above steps of selecting a desired treatment procedure, checking if the new component fits with the selected treatment procedure, and signaling if the new component does not fit with the selected treatment procedure are performed before the step of coupling the new component with the apparatus.

6. Method according to claim 2, the step of verifying comprises the steps of:
   determining the category of the new component,
   checking if a component of the same category was detected before,
   checking if a component is engaged with the engaging means of the type adapted to receive the components of the category of the new component.

7. Method according to claim 2, the step of verifying comprises the steps of:
   determining the category of the new component,
   checking if a component is engaged with the engaging means of the type adapted to receive the components of the category of the new component.

8. Method according to claim 1, wherein said components comprise a plurality of components of different categories, each component of a same category having respective mechanical connection to a corresponding operating area on the apparatus, different from that of components of other categories.

9. Method according to claim 8, wherein said apparatus includes a plurality of different types of engaging means, each type of engaging means being designed for mechanically engaging, in a respective operating area, a component of one corresponding category only.

10. Method according to claim 1, wherein the above steps of reading and verifying are repeated for any new component to be installed.

11. Method according to claim 1, wherein the information comprises one or more selected in the group including:
    Identity of the component,
    Identity of a series of identical components,
    Expiration date of the component,
    Manufacturer,
    One or more commands for programming the apparatus to execute a procedure on said fluid,
    Data concerning a patient.

12. Method according to claim 1, wherein the information carrier is one selected in the group comprising: a surface of the component, a packaging of the component, a card associated with the component.

13. Method according to claim 1, comprising the step of entering commands into the apparatus for carrying out a corresponding procedure on said fluid, said step of entering commands including the following sub-steps:
    Associating a command information to a readable information carrier,
    Relatively approaching to one another the information carrier and the reading portion to enter the command in the apparatus,
    Initiating a treatment procedure complying with the entered command.

14. Method according to claim 1, comprising the step of entering patient data into the apparatus, said step of entering patient data including the following sub-steps:
    Associating patient data information to a readable information carrier,
    Relatively approaching to one another the information carrier and the reading portion to enter the command in the apparatus.

15. Method according to claim 1, comprising an additional procedure for installing a new replaceable component on the apparatus without interacting with said reader, said additional procedure including the following steps:
    entering the information of a new component to be installed on the apparatus by acting on said user interface,
    verifying if the new component is of the same category of a component already installed on the machine,
    displaying on said screen a message informing if a component of the same category is already installed,
    coupling the new component with the apparatus in correspondence of a respective of said operating areas, the component when coupled leaving the reading portion accessible for reading the information.

16. Method according to claim 15, wherein said step of entering information by acting on the user interface comprises the steps of:

a. Configuring the user interface as a plurality of displays, each display being accessible to the operator and including information corresponding to at least a respective replaceable component,
b. Selecting the desired display of the user interface,
c. Selecting the new component to be installed by acting on said selected display.

17. Method according to claim 15, comprising a step of entering commands using said user interface and without acting on said reader.

18. Method according to claim 15, comprising a step of entering patient related information using said user interface and without acting on said reader.

19. Method according to claim 1, wherein for reading the information, the carrier of said information is and the reading portion are approached to a distance less then 30 cm.

20. Method according to claim 1, before the reading portion can read any information, a step is provided for activation of said reading portion.

21. Method according to claim 1, after the reading portion has read any information, a step is provided for de-activation of said reading portion.

22. Method according to claim 1, wherein the reading portion is deactivated when at least one of the following circumstances occurs:
the reading portion reads no information for a prefixed timeout period,
a user turns the reading portion off by acting of the user interface,
a specific procedure not requiring use of the reading portion is selected by the user,
a specific procedure not requiring use of the reading portion is initiated by the apparatus.

23. Method according to claim 1, wherein the reading portion is activated when at least one of the following circumstances occurs:
the apparatus is turned on,
a user turns the reading portion on by acting on the user interface,
a specific procedure requiring use of the reading portion is selected by the user,
a specific procedure requiring use of the reading portion is initiated by the apparatus.

24. Fluid processing medical apparatus, comprising:
a support structure,
a plurality of replaceable components of different categories engaged to the support structure in
correspondence of respective operating areas,
at least a user interface enabling setting of a plurality of parameters pertinent to operation of said apparatus or pertinent to a process to be performed by said apparatus, the user interface including at least a screen,
a reader, distinct from said user interface, having a reading portion for reading information concerning the components, the reading portion being spaced from said operating areas and accessible for reading the information irrespective of the components being engaged or not to the support structure,
a control system for controlling operation of said medical apparatus and responsive to actions by a user on said user interface, said control system also communicating with the reader and being programmed for receiving and storing at least said information concerning the components every time the reader reads information concerning a new component to be installed on the apparatus, wherein the control system is programmed for verifying if the new component is of the same category of a component already installed on the machine, and wherein the step of verifying comprises the steps of:
determining the category of the new component,
checking if a component of the same category was detected before,
checking if a component is engaged with the engaging means of the type adapted to
receive the components of the category of the new component.

25. Apparatus according to claim 24, wherein said components comprise a plurality of components of different categories, each component of a same category having respective mechanical connection to a corresponding operating area on the apparatus, different from that of components of other categories.

26. Apparatus according to claim 25, wherein said apparatus includes a plurality of different types of engaging means, each type of engaging means being designed for mechanically engaging, in a respective operating area, a component of one corresponding category only.

27. Apparatus according to claim 24, wherein the control system is also programmed for signaling that a component of the same category is already installed on the apparatus.

28. Apparatus according to claim 27, wherein the control system is programmed for executing the following steps, after the signaling step:
requesting for confirmation to substitute the installed component with the new component,
initiating a procedure for substitution of the installed component with the new component.

29. Apparatus according to claim 24, wherein the control system is programmed for executing the following steps:
receiving selection of a desired treatment procedure,
checking if the new component fits with the selected treatment procedure,
signaling if the new component does not fit with the selected treatment procedure.

30. Apparatus according to claim 24, wherein the control system is programmed for repeating the above steps of reading and verifying anytime the reader reads information of a new component to be installed.

31. Apparatus according to claim 24, wherein the information comprises one or more selected in the group including:
Identity of the component,
Identity of a series of identical components,
Expiration date of the component,
Manufacturer,
One or more commands for programming the apparatus to execute a procedure on said fluid,
Data concerning a patient.

32. Apparatus according to claim 24, wherein the information carrier is one selected in the group comprising: a surface of the component, a packaging of the component, a card associated with the component.

33. Apparatus according to claim 24, wherein the control system is programmed for receiving commands for carrying out a corresponding procedure on said fluid by reading a command information associated to a readable information carrier which is approached to the reading portion.

34. Apparatus according to claim 24, wherein the reader comprises an optical reader or a radio-frequency reader adapted to detect said information when the component and the reading portion are approached one another at a distance less then 30 cm.

35. Apparatus according to claim 24, wherein the user interface comprises a means for receiving an entry addressed to turn on or off the reading portion, said control system being programmed for:
receiving said entry, and
respectively turning on or off the reading portion depending upon the entry.

36. Apparatus according to claim 24, wherein the control system is programmed for:
receiving a information concerning a fluid treatment procedure selected by a user,
verifying if the selected fluid treatment procedure requires or not use of the reading portion de-activating said reading portion, when the selected treatment procedure does not require use of the reading portion.

37. Apparatus according to claim 24, wherein the control system is programmed for de-activating said reading portion, when the reading portion reads no information during a pre-fixed timeout period.

38. Apparatus according to claim 24, wherein the control system is programmed for:
receiving a information concerning a fluid treatment procedure selected by a user,
verifying if the selected fluid treatment procedure requires or not use of the reading portion activating said reading portion, when the selected treatment procedure does require use of the reading portion.

39. Apparatus according to claim 24, wherein the control system is programmed for activating said reading portion, when the apparatus is turned on.

40. Method for setting-up a fluid processing medical apparatus, the apparatus being of the type comprising:
a support structure for receiving a plurality of replaceable components of different categories in correspondence of respective operating areas of said apparatus,
at least a user interface for enabling setting of a plurality of parameters pertinent to operation of said apparatus or pertinent to a process to be performed by said apparatus, the user interface including at least a screen,
the method comprising the following steps:
providing a reader having a reading portion for reading information concerning the components, the reading portion being distinct and spaced from said operating areas and accessible for reading the information irrespective of the components being engaged or not with apparatus,
reading the information of a new component to be installed on the apparatus by relatively approaching the reading portion to a carrier of said new component information,
coupling the new component with the apparatus in correspondence of a respective of said operating areas, the component when coupled leaving the reading portion accessible for reading the information, wherein after the reading step it is provided a step of verifying if the new component is of the same category of a component already installed on the apparatus, and wherein the step of verifying comprises the steps of:
determining the category of the new component,
checking if a component of the same category was detected before,
checking if a component is engaged with the engaging means of the type adapted to
receive the components of the category of the new component.

41. Method for setting-up a fluid processing medical apparatus, the apparatus being of the type comprising:
a support structure for receiving a plurality of replaceable components of different categories in correspondence of respective operating areas of said apparatus,
at least a user interface for enabling setting of a plurality of parameters pertinent to operation of said apparatus or pertinent to a process to be performed by said apparatus, the user interface including at least a screen,
the method comprising the following steps:
providing a reader having a reading portion for reading information concerning the components, the reading portion being distinct and spaced from said operating areas and accessible for reading the information irrespective of the components being engaged or not with apparatus,
reading the information of a new component to be installed on the apparatus by relatively approaching the reading portion to a carrier of said new component information,
coupling the new component with the apparatus in correspondence of a respective of said operating areas, the component when coupled leaving the reading portion accessible for reading the information, the method further comprising the step of entering commands into the apparatus for carrying out a corresponding procedure on said fluid, said step of entering commands including the following sub-steps:
Associating a command information to a readable information carrier,
Relatively approaching to one another the information carrier and the reading portion to enter the command in the apparatus,
Initiating a treatment procedure complying with the entered command.

42. Method for setting-up a fluid processing medical apparatus, the apparatus being of the type comprising:
a support structure for receiving a plurality of replaceable components of different categories in correspondence of respective operating areas of said apparatus,
at least a user interface for enabling setting of a plurality of parameters pertinent to operation of said apparatus or pertinent to a process to be performed by said apparatus, the user interface including at least a screen,
the method comprising the following steps:
providing a reader having a reading portion for reading information concerning the components, the reading portion being distinct and spaced from said operating areas and accessible for reading the information irrespective of the components being engaged or not with apparatus,
reading the information of a new component to be installed on the apparatus by relatively approaching the reading portion to a carrier of said new component information,
coupling the new component with the apparatus in correspondence of a respective of said operating areas, the component when coupled leaving the reading portion accessible for reading the information, the method further comprising the step of entering patient data into the apparatus, said step of entering patient data including the following sub-steps:
Associating patient data information to a readable information carrier,
Relatively approaching to one another the information carrier and the reading portion to enter the command in the apparatus.

43. Fluid processing medical apparatus, comprising:
a support structure, a plurality of replaceable components of different categories engaged to the support structure in correspondence of respective operating areas, at least a user interface enabling setting of a plurality of parameters pertinent to operation of said apparatus or pertinent to a process to be performed by said apparatus, the user interface including at least a screen, a reader, distinct from said user interface, having a reading portion for reading information concerning the components, the reading portion being spaced from said operating areas and accessible for reading the information irrespective of the components being engaged or not to the support structure, a control system for controlling operation of said medical apparatus and responsive to actions by a user on said user interface, said control system also communicating with the reader and being programmed for receiving and storing at least said information concerning the components every time the reader reads information concerning a new component to be installed on the apparatus, wherein the control system is programmed for executing the following steps:

receiving selection of a desired treatment procedure, checking if the new component fits with the selected treatment procedure, signaling if the new component does not fit with the selected treatment procedure.

44. Apparatus according to claim 43, wherein the control system is programmed for allowing the step of coupling the new component with the apparatus only after the step of checking if the new component fits with the selected treatment procedure.

45. Fluid processing medical apparatus, comprising:

a support structure, a plurality of replaceable components of different categories engaged to the support structure in correspondence of respective operating areas, at least a user interface enabling setting of a plurality of parameters pertinent to operation of said apparatus or pertinent to a process to be performed by said apparatus, the user interface including at least a screen, a reader, distinct from said user interface, having a reading portion for reading information concerning the components, the reading portion being spaced from said operating areas and accessible for reading the information irrespective of the components being engaged or not to the support structure, a control system for controlling operation of said medical apparatus and responsive to actions by a user on said user interface, said control system also communicating with the reader and being programmed for receiving and storing at least said information concerning the components every time the reader reads information concerning a new component to be installed on the apparatus, wherein the control system is programmed for receiving commands for carrying out a corresponding procedure on said fluid by reading a command information associated to a readable information carrier which is approached to the reading portion.

46. Apparatus according to claim 45, wherein the control system is programmed for receiving patient data by reading data carried by a readable information carrier which is approached to the reading portion.

47. Apparatus according to claim 46, wherein the control system is programmed for executing an additional procedure for installing a new replaceable component on the apparatus without interacting with said reader, the additional procedure comprising the steps of:

allowing to enter information of a new component to be installed on the apparatus by acting on said user interface, verifying if the new component is of the same category of a component already installed on the machine, displaying on said screen a message informing if a component of the same category is already installed, coupling the new component with the apparatus in correspondence of a respective of said operating areas, the component when coupled leaving the reading portion accessible for reading the information.

48. Apparatus according to claim 47, wherein said step of allowing entering information by acting on the user interface comprises the steps of:

Configuring the user interface as a plurality of displays, each display being accessible to the operator and including information corresponding to at least a respective replaceable component, Allowing selecting the desired display of the user interface, Allowing selecting the new component to be installed by acting on said selected display.

49. Fluid processing medical apparatus, comprising:

a support structure, a plurality of replaceable components of different categories engaged to the support structure in correspondence of respective operating areas, at least a user interface enabling setting of a plurality of parameters pertinent to operation of said apparatus or pertinent to a process to be performed by said apparatus, the user interface including at least a screen, a reader, distinct from said user interface, having a reading portion for reading information concerning the components, the reading portion being spaced from said operating areas and accessible for reading the information irrespective of the components being engaged or not to the support structure, a control system for controlling operation of said medical apparatus and responsive to actions by a user on said user interface, said control system also communicating with the reader and being programmed for receiving and storing at least said information concerning the components every time the reader reads information concerning a new component to be installed on the apparatus, wherein the control system is programmed for:

receiving a information concerning a fluid treatment procedure selected by a user, verifying if the selected fluid treatment procedure requires or not use of the reading portion de-activating said reading portion, when the selected treatment procedure does not require use of the reading portion.

50. Fluid processing medical apparatus, comprising:

a support structure, a plurality of replaceable components of different categories engaged to the support structure in correspondence of respective operating areas, at least a user interface enabling setting of a plurality of parameters pertinent to operation of said apparatus or pertinent to a process to be performed by said apparatus, the user interface including at least a screen, a reader, distinct from said user interface, having a reading portion for reading information concerning the components, the reading portion being spaced from said operating areas and accessible for reading the information irrespective of the components being engaged or not to the support structure, a control system for controlling operation of said medical apparatus and responsive to actions by a user on said user interface, said control system also communicating with the reader and being programmed for receiving and storing at least said information concerning the components every time the reader reads information concerning a new component to be installed on the apparatus, wherein the control system is programmed for:

receiving a information concerning a fluid treatment procedure selected by a user, verifying if the selected fluid treatment procedure requires or not use of the reading portion activating said reading portion, when the selected treatment procedure does require use of the reading portion.

* * * * *

UNITED STATES PATENT AND TRADEMARK OFFICE
CERTIFICATE OF CORRECTION

PATENT NO.        : 8,267,308 B2                                       Page 1 of 1
APPLICATION NO.   : 12/596070
DATED             : September 18, 2012
INVENTOR(S)       : Jacky Devergne et al.

It is certified that error appears in the above-identified patent and that said Letters Patent is hereby corrected as shown below:

At column 17, line 42, claim 4, after "claim 3,", please delete "herein" and insert therefor --wherein--.

Signed and Sealed this
Eleventh Day of December, 2012

David J. Kappos
*Director of the United States Patent and Trademark Office*